(12) United States Patent
Chen et al.

(10) Patent No.: US 12,331,329 B2
(45) Date of Patent: *Jun. 17, 2025

(54) GENOME EDITING IN PLANTS

(71) Applicant: Monsanto Technology LLC, St. Louis, MO (US)

(72) Inventors: Yurong Chen, Chesterfield, MO (US); Annie Saltarikos, O'Fallon, MO (US); Jianping Xu, Chesterfield, MO (US); Xudong Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/045,747

(22) PCT Filed: May 24, 2019

(86) PCT No.: PCT/US2019/033984
§ 371 (c)(1),
(2) Date: Oct. 6, 2020

(87) PCT Pub. No.: WO2019/227030
PCT Pub. Date: Nov. 28, 2019

(65) Prior Publication Data
US 2021/0054390 A1 Feb. 25, 2021

Related U.S. Application Data

(60) Provisional application No. 62/676,228, filed on May 24, 2018.

(51) Int. Cl.
*C12N 15/82* (2006.01)
*C12N 9/22* (2006.01)
*C12N 15/113* (2010.01)

(52) U.S. Cl.
CPC .......... *C12N 9/22* (2013.01); *C12N 15/8201* (2013.01); *C12N 15/8213* (2013.01); *C12N 15/113* (2013.01); *C12N 15/8205* (2013.01); *C12N 2310/20* (2017.05)

(58) Field of Classification Search
CPC ................. C12N 15/8213; C12N 2310/20
See application file for complete search history.

(56) References Cited

U.S. PATENT DOCUMENTS

| | | | |
|---|---|---|---|
| 5,484,956 | A | 1/1996 | Lundquist et al. |
| 5,631,152 | A | 5/1997 | Fry et al. |
| 8,362,317 | B2 * | 1/2013 | Calabotta .......... C12N 15/8205 800/278 |
| 2016/0264981 | A1 | 9/2016 | Yang et al. |
| 2016/0264983 | A1 | 9/2016 | Martinell et al. |
| 2017/0114351 | A1 | 4/2017 | Mahfouz et al. |
| 2017/0121722 | A1 * | 5/2017 | Anand ................. A01H 4/008 |
| 2018/0073035 | A1 | 3/2018 | Gao et al. |
| 2021/0238613 | A1 * | 8/2021 | Chen ................. C12N 15/8209 |

FOREIGN PATENT DOCUMENTS

| | | | |
|---|---|---|---|
| CA | 2996329 | | 4/2017 |
| CA | 3025828 | | 12/2017 |
| WO | 97/12046 | A1 | 4/1997 |
| WO | 99/51759 | A1 | 10/1999 |
| WO | 2015116969 | | 8/2015 |
| WO | 2016184989 | A1 | 11/2016 |
| WO | 2018005491 | A1 | 1/2018 |
| WO | WO2018005491 | | 1/2018 |
| WO | WO2018085693 | | 5/2018 |
| WO | WO-2018085693 | A1 * | 5/2018 ............... A01H 1/06 |

OTHER PUBLICATIONS

Hwang et al (Agrobacterium-mediated plant transformation: biology and applications. American Society of Plant Biologists. 1-31, 2017) (Year: 2017).*
Hamada et al. An in planta biolistic method for stable wheat transformation. Scientific Report. 1-8, 2017. (Year: 2017).*
Patnaik et al (Agrobacterium-mediated transformation of mature embryos of Triticum aestivum and Triticum durum. Current Science. 91, 307-317, 2006). (Year: 2006).*
Of Liang et al (Selection of highly efficient sgRNAs for CRISPR/Cas9-based plant genome editing. Nature Scientific Reports, 1-8, 2016). (Year: 2016).*
Lowe et al (Rapid genotype "independent" *Zea mays* L. (maize) transformation via direct somatic embryogenesis. In Vitro Cellular & Developmental Biology—Plant 54:240-252, published online 2018.4). (Year: 2018).*
Begemann et al (Precise insertion and guided editing of higher plant genomes using Cpf1 CRISPR nucleases. Nature Scientific Reports. 1-6, 2017) (Year: 2017).*
Liang et al (Selection of highly efficient sgRNAs for CRISPR/Cas9-based plant genome editing. Nature Scientific Reports, 1-8, 2016). (Year: 2016).*
Rech et al (High-efficiency transformation by biolistics of soybean, common bean and cotton transgenic plants. Nature Protocols. 410-417, 2008). (Year: 2008).*
Svitashev et al (Targeted Mutagenesis, Precise Gene Editing, and Site-Specific Gene Insertion in Maize Using Cas9 and Guide RNA. Plant Physiology. Vol. 169, pp. 931-994, 2015). (Year: 2015).*
Wang et al (Effects of Environmental Temperature on the Regeneration Frequency of the Immature Embryos of Wheat (*Triticum aestivum* L.) Journal of Integrative Agriculture, 13(4): 722-732, 2014). (Year: 2014).*

(Continued)

*Primary Examiner* — Charles Logsdon
*Assistant Examiner* — Wayne Zhong
(74) *Attorney, Agent, or Firm* — Dentons US LLP; Jan Desomer

(57) ABSTRACT

Provided are compositions for genome editing and site-directed integration in plants comprising microprojectile particles coated, treated of applied with a recombinant DNA construct comprising a sequence encoding one or more genome editing reagents for delivery to a mature embryo explant from dry seeds. Further provided are methods for genome editing and site-directed integration in at least one cell of a plant using the disclosed compositions, and plants, plant parts and seeds comprising an edited genome or site-directed integration, which are produced by the disclosed methods.

25 Claims, 2 Drawing Sheets
Specification includes a Sequence Listing.

(56) References Cited

OTHER PUBLICATIONS

U.S. Appl. No. 17/049,326, filed Oct. 20, 2020, Chen et al.
Svitashev, S., et al. "Genome editing in maize directed by CRISPR-Cas9 ribonucleoprotein complexes," Nature Communications. 7:13274 (2016).
International Search Report and Written Opinion for International Application No. PCT/US2019/033976 mailed Aug. 19, 2019.
USPTO: Restriction Requirement regarding U.S. Appl. No. 17/049,326, dated Sep. 27, 2021.
USPTO: Response to Restriction Requirement regarding U.S. Appl. No. 17/049,326, filed Dec. 7, 2021.
Helenius et al. "Optimization of Gene Delivery into *Arabidopsis*, Tobacco, and Birch Using the Helios Gene Gun System," Bio-Rad Particle Delivery Systems, Tech Note 2453, Jan. 20, 2012 (Jan. 20, 2012), pp. 1-6. Retrieved from the Internet:<www.bio-rad.com/webroot/web/pdf/lsr/literature/Bulletin_2453.pdf> on Jul. 11, 2019.
International Search Report and Written Opinion for International Application No. PCT/US2019/033984 mailed Aug. 23, 2019.
USPTO: Response to Non-Final Office Action regarding U.S. Appl. No. 17/049,326, filed Jul. 18, 2022.
USPTO: Non-Final Office Action regarding U.S. Appl. No. 17/049,326, dated Mar. 1, 2022.
Yau et al., Less is more: strategies to remove maker genes from transgenic plants, BMC Technology 13:36, 2013.
USPTO: Advisory Action regarding U.S. Appl. No. 17/049,326, mailed Feb. 1, 2023.
USPTO: Response to Final Office Action regarding U.S. Appl. No. 17/049,326, filed Feb. 1, 2023.
USPTO: Final Office Action regarding U.S. Appl. No. 17/049,326, mailed Oct. 25, 2022.
USPTO: Response to Final Office Action regarding U.S. Appl. No. 17/049,326, filed Dec. 30, 2022.
USPTO: Non-Final Office Action regarding U.S. Appl. No. 17/049,326, mailed Apr. 20, 2023.
USPTO: Response to Non-Final Office Action regarding U.S. Appl. No. 17/049,326, filed Jul. 5, 2023.
USPTO: Response to Final Office Action regarding U.S. Appl. No. 17/049,326, filed Nov. 13, 2023.
USPTO: Examiner Interview Summary U.S. Appl. No. 17/049,326, filed Nov. 17, 2023.
USPTO: Final Office Action regarding U.S. Appl. No. 17/049,326, dated Aug. 2, 2023.
USPTO: Response to Non-Final Office Action regarding U.S. Appl. No. 17/049,326, filed Mar. 13, 2024.
USPTO: Response to Final Office Action regarding U.S. Appl. No. 17/049,326, filed Jun. 20, 2024.
USPTO: Final Office Action regarding U.S. Appl. No. 17/049,326, mailed May 21, 2024.
USPTO: Non-Final Office Action regarding U.S. Appl. No. 17/049,326, mailed Nov. 4, 2024.
USPTO: Response to Non-final Office Action regarding U.S. Appl. No. 17/049,326, filed Feb. 20, 2025.

\* cited by examiner

SEQUENCE LISTING

<160> NUMBER OF SEQ ID NOS: 11

<210> SEQ ID NO 1
<211> LENGTH: 698
<212> TYPE: DNA
<213> ORGANISM: Glycine max

<400> SEQUENCE: 1

```
ctacgcatta ggaattcctt tctttgtgat taaatagatg tacacatctc aatgcttgat      60
tacattgtat tgtgacagtc ctcctgtgtc ggtaaggaaa aaagttatgg aattttagga     120
tcttcaattt ttgctgaaat ttcaaataaa aggtatcctg atatcatgtt ggatatttaa     180
agacaaaaaa atttgtaaac taatctttgc acattagttt tggcctctct gcctattgga     240
ttgatgcatg tttcattatt gcaggattgg ctggtttatc aactgcaaaa tatttggctg     300
atgctgggca taaacctata ttgctggaag caagagacgt tctaggtgga aaggttttcc     360
tgctaattta atctcttacg tcaattagtt gtcactttgt gtgcattctg ctcattattt     420
tagcatgctg tttaatgaaa taagaaattt gtttgtgttg ttccgtcata atctatttga     480
tgtgttggct ttataacttc atcatcaggc ttgttgaaga ttaccgcagt aatgtaaaac     540
atatttataa taaatcaatt ttgatgcatt gtgttttac actattgttt cattttctaa     600
ggttgctgca tggaaagaca aggatggaga ctggtatgag acaggtctac acatcttctg     660
taagttcatt aaaatctcgg gtttaacttt tttttttt                             698
```

<210> SEQ ID NO 2
<211> LENGTH: 646
<212> TYPE: DNA
<213> ORGANISM: Glycine max

<400> SEQUENCE: 2

```
ctacgcatta ggaatttcct tctttgtgat taaatagatg tacgcatctc aatgcttgat      60
tacattgtgt tgtgacagtc ctgtgtcggt aaggaaaaaa gttatggaat tttaggtacc     120
ctgatatcat gttggatatt taaagactaa tctttgcaca ttagttttgg cctctctgtc     180
tattggattg atgcatgttt caaattatcg caggattggc tggtttatca actgcaaaat     240
atttggctga tgctgggcat aaacctatat tgctggaagc aagagacgtt ctaggtggaa     300
aggttttcct gctaatttaa tccctttcgg caataagttg tcacttagtg cgccttcttt     360
tcattatttt aacaagctgt ttaatgaaat aagaaatttg tttgtgttgt tccatcataa     420
tctatttgat gcgttggctt tataacttca tcatcaggtt tgttgaaggt taccacagta     480
tatacaacat atttataata aatcaatttt aatgtattgt gttttatac tattgtttca      540
ttttctaagg ttgctgcatg gaaagacaag gatggagact ggtacgagac aggcctacac     600
atcttttgta agttcattaa aatcttgggt ttaactcttt tttttt                    646
```

<210> SEQ ID NO 3
<211> LENGTH: 80
<212> TYPE: DNA
<213> ORGANISM: Artificial Sequence
<220> FEATURE:
<223> OTHER INFORMATION: Synthetic

<400> SEQUENCE: 3

```
gttttagagc tagaaatagc aagttaaaat aaggctagtc cgttatcaac ttgaaaaagt      60
acgatgttca agggttttag                                                  80
```

<210> SEQ ID NO 4
<211> LENGTH: 80
<212> TYPE: DNA
<213> ORGANISM: Artificial Sequence
<220> FEATURE:
<223> OTHER INFORMATION: Synthetic

<400> SEQUENCE: 4

```
gttttagagc tagaaatagc aagttaaaat aaggctagtc cgttatcaac ttgaaaaagt      60
gaagcaagag acgttctagg                                                  80
```

<210> SEQ ID NO 5
<211> LENGTH: 80
<212> TYPE: DNA
<213> ORGANISM: Artificial Sequence
<220> FEATURE:
<223> OTHER INFORMATION: Synthetic

<400> SEQUENCE: 5

```
gttttagagc tagaaatagc aagttaaaat aaggctagtc cgttatcaac ttgaaaaagt      60
tctgagctac tagctactcg                                                  80
```

```
<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
tcctgtgtcg gtaaggaaaa aag                                          23

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
cctgatgatg aagttataaa gccaac                                       26

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
tcctgtgtcg gtaaggaaaa aag                                          23

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gatttcacgg gttggggttt c                                            21

<210> SEQ ID NO 10
<211> LENGTH: 58
<212> TYPE: DNA
<213> ORGANISM: Artificial Sequence
<220> FEATURE:
<223> OTHER INFORMATION: Synthetic

<400> SEQUENCE: 10
tttatctttg tttctccgtt gatagggtac caaaaaaaaa gcaccgactc ggtgccac    58

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
cctgatgatg aagttataaa gccaac                                       26
```

GENOME EDITING IN PLANTS

CROSS-REFERENCE TO RELATED APPLICATIONS

This application is a 371 National Stage application of International Application No. PCT/US2019/033984, which claims the benefit of United States Provisional Application No. 62/676,228 filed May 24, 2018, each of which is herein incorporated by reference in its entirety.

INCORPORATION OF SEQUENCE LISTING

The sequence listing that is contained in the file named "MONS444WO_ST25.txt," which is 4 kilobytes as measured in Microsoft Windows operating system and was created on May 23, 2019, is filed electronically herewith and incorporated herein by reference.

FIELD OF THE INVENTION

The present disclosure relates to compositions for genome editing in plants with a DNA molecule encoding a genome editing reagent, and methods of their use.

BACKGROUND

Precise genome editing technologies have promised to be powerful tools for engineering gene expression and function, with the potential of improving agriculture. A continuing need exists in the art for the development of novel compositions and methods that can be used to effectively and efficiently edit the genome of a plant.

SUMMARY OF THE INVENTION

The present disclosure provides a method of editing a genome of a plant, comprising delivering to a mature plant embryo explant a recombinant DNA construct comprising a sequence encoding a site-specific nuclease, wherein the sequence is operably linked to a plant-expressible promoter, and regenerating a plant from the mature plant embryo explant, wherein the regenerated plant comprises an edit or a site-directed integration at or near the target site of the site-specific nuclease in the genome of at least one cell of the regenerated plant. In certain embodiments the recombinant DNA construct is delivered to the mature plant embryo explant via bacterially mediated transformation. In other embodiments the recombinant DNA construct is delivered to the mature plant embryo explant via *Agrobacterium* mediated transformation. In some embodiments a T-DNA transformation vector comprising the recombinant DNA construct is delivered to the mature plant embryo explant.

In additional embodiments the recombinant DNA construct is delivered to the mature plant embryo explant via particle bombardment. In some embodiments, a particle coated or applied with the recombinant DNA construct is delivered to the mature plant embryo explant via particle bombardment. In certain embodiments the particle is a tungsten, platinum or gold particle. In other embodiments the particle has a size of between about 0.5 µm and about 1.5 µm. In yet other embodiments the particle has a size of about 0.6 µm, about 0.7 µm, or about 1.3 µm. In some embodiments a plurality of particles coated or applied with the recombinant DNA molecule are delivered to the mature plant embryo explant via particle bombardment. In certain embodiments the amount of particles delivered to the explant is between about 50 µg and about 5000 µg, or between about 50 µg and about 5000 µg, or between about 50 µg and about 2000 µg, or between about 50 µg and about 1000 µg, or between about 50 µg and about 500 µg, or between about 100 µg and about 500 µg.

In certain embodiments the method further comprises identifying a regenerated plant having at least one cell comprising the edit or site-directed integration at or near the target site of the site-specific nuclease. In some embodiments the identifying step comprises identifying a regenerated plant having the edit or site-directed integration based on a phenotype or trait. In other embodiments the identifying step comprises identifying a regenerated plant having the edit or site-directed integration based on a molecular assay.

In further embodiments the site-specific nuclease is a guided nuclease, such as a CRISPR associated protein. In other embodiments the particle is further coated or applied with a guide nucleic acid. In some embodiments the guided nuclease is Cas1, Cas1B, Cas2, Cas3, Cas4, Cas5, Cas6, Cas7, Cas8, Cas9, Csn1, Csx12, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, CasZ, or Argonaute protein, or a homolog or modified version thereof. In yet other embodiments the guided nuclease is a Cas9 protein. In still other embodiments the Cas9 protein is from *Streptococcus pyogenes*. In additional embodiments the guided nuclease is a Cpf1 protein. In certain embodiments the site-specific nuclease is not a guided nuclease. In some embodiments the site-specific nuclease is a meganuclease, a zinc-finger nuclease (ZFN), a recombinase, a transposase, or a transcription activator-like effector nuclease (TALEN).

In certain embodiments the delivering step further comprises delivering a second recombinant DNA construct or molecule to the mature plant embryo explant. In some embodiments the particle is further coated or applied with a second recombinant DNA construct or molecule. In additional embodiments the second recombinant DNA construct or molecule is a donor template. In other embodiments the donor template comprises a homology sequence comprising a mutation for introduction of the mutation in the genome of the plant at or near the target site of the site-specific nuclease through template-mediated repair. In yet other embodiments the donor template comprises an insertion sequence and at least one homology sequence for integration of the insertion sequence into the genome of the plant at or near the target site of the site-specific nuclease.

In particular embodiments the insertion sequence comprises a transgene comprising a coding sequence or a transcribable DNA sequence operably linked to a plant-expressible promoter. In certain embodiments the transgene comprises a gene of interest. In some embodiments the transgene comprises a protein coding sequence. In other embodiments the transgene comprises a transcribable DNA sequence encoding a non-coding RNA molecule. In yet other embodiments the transgene comprises a marker gene. In further embodiments the second recombinant DNA molecule comprises a marker gene. In certain embodiments the marker gene is a selectable marker gene. In some embodiments the selectable marker gene comprises an adenylyltransferase (aadA) gene, a neomycin phosphotransferase (nptII) gene, a hygromycin phosphotransferase (hpt, hph or aph IV), 5-enolpyruvylshikimate-3-phosphate synthase (EPSPS) gene, a dicamba monooxygenase (DMO) gene, or a bialaphos resistance (bar) or phosphinothricin N-acetyltransferase (pat) gene. In another embodiment the selectable marker gene comprises an adenylyltransferase (aadA) gene. In additional embodiments the marker gene is a screenable marker gene. In various embodiments the screenable marker gene comprises a green fluorescent protein (GFP) or a β-glucuronidase (GUS) gene.

In further embodiments the second recombinant DNA construct or molecule comprises a donor template region and a transgene comprising a coding sequence or a transcribable DNA sequence, wherein the transgene is located outside of the donor template region of the second recombinant DNA construct or molecule. In some embodiments the second recombinant DNA construct or molecule comprises a transcribable DNA sequence encoding a guide nucleic acid, wherein the transcribable DNA sequence is operably linked to a plant-expressible promoter. In certain embodiments the recombinant DNA construct further comprises a marker gene. In some embodiments the marker gene is a selectable marker gene. In various embodiments the selectable marker gene comprises an adenylyltransferase (aadA) gene, a neomycin phosphotransferase (nptII) gene, a hygromycin phosphotransferase (hpt, hph or aph IV), 5-enolpyruvylshikimate-3-phosphate synthase (EPSPS) gene, a dicamba monooxygenase (DMO) gene, or a bialaphos resistance (bar) or phosphinothricin N-acetyltransferase (pat) gene. In another embodiment the selectable marker gene comprises an adenylyltransferase (aadA) gene. In other embodiments the marker gene is a screenable marker gene. In yet other embodiments the screenable marker gene comprises a green fluorescent protein (GFP) or a β-glucuronidase (GUS) gene.

In some embodiments the recombinant DNA construct further comprises a transcribable DNA sequence encoding a guide nucleic acid, wherein the transcribable DNA sequence is operably linked to a second plant-expressible promoter. In other embodiments the recombinant DNA construct further comprises a donor template region. In certain embodiments the donor template region comprises a homology sequence comprising a mutation for introduction of the mutation in the genome of the plant at or near the target site of the site-specific nuclease through template-mediated repair. In yet other embodiments the donor template region comprises an insertion sequence and at least one homology sequence for integration of the insertion sequence into the genome of the plant at or near the target site of the site-specific nuclease. In still other embodiments the insertion sequence comprises a transgene comprising a coding sequence or a transcribable DNA sequence operably linked to a plant-expressible promoter. In additional embodiments the transgene comprises a gene of interest. In particular embodiments the transgene comprises a protein coding sequence. In some embodiments the transgene comprises a transcribable DNA sequence encoding a non-coding RNA molecule. In certain embodiments the transgene comprises a marker gene.

In additional embodiments the method further comprises selecting a regenerated plant having a marker gene, wherein the marker gene is co-delivered with the recombinant DNA molecule. In some embodiments the marker gene is a selectable marker gene. In other embodiments the selecting step comprises treating the mature embryo explant, or a shoot and/or root culture or plantlet regenerated therefrom, with a selection agent. In certain embodiments the selectable marker gene is an adenylyltransferase (aadA) gene.

Several embodiments relate to a method of editing a genome of a plant, comprising: a) delivering to a mature plant embryo explant a recombinant DNA construct comprising a sequence encoding one or more genome editing reagents, wherein the sequence is operably linked to a plant-expressible promoter; and b) regenerating a plant from the mature plant embryo explant, wherein the regenerated plant comprises an edit or site-directed integration at or near the target site in the genome of at least one cell of the regenerated plant. In some embodiments, the method further comprises identifying a regenerated plant having at least one cell comprising the edit or site-directed integration at or near the target site. In some embodiments, the method further comprises selecting a regenerated plant having a marker gene, wherein the marker gene is co-delivered with the recombinant DNA molecule. In some embodiments, the recombinant DNA construct is delivered to the mature plant embryo explant via bacterially mediated transformation. In some embodiments, the recombinant DNA construct is delivered to the mature plant embryo explant via *Agrobacterium* mediated transformation. In some embodiments, the recombinant DNA construct is delivered to the mature plant embryo explant in a T-DNA transformation vector. In some embodiments, the recombinant DNA construct is delivered to the mature plant embryo explant via particle bombardment. In some embodiments, the particle is a tungsten, platinum or gold particle. In some embodiments, the particle has a size of about 0.5 µm, about 0.6 µm, about 0.7 µm, about 0.8 µm, about 0.9 µm, about 1 µm, 1.1 µm, about 1.2 µm, about 1.3 µm, about 1.4 µm, or about 1.5 µm. In some embodiments, the particle is further coated or applied with a second recombinant DNA construct or molecule. In some embodiments, the second recombinant DNA construct or molecule is a donor template.

In certain embodiments the plant is a dicot plant. In particular embodiments the plant is a soybean plant. In other embodiments the plant is a monocot plant. In additional embodiments the mature embryo explant comprises, prior to the delivering step, one or more of the following: (i) a guide nucleic acid, (ii) a polynucleotide comprising a transgene or marker gene, (iii) a polynucleotide comprising a transgene encoding a non-coding RNA molecule or guide nucleic acid, and/or (iv) a donor template. In some embodiments the mature embryo explant is a dry excised explant. In other embodiments the mature embryo explant is a wet, dried wet or wet excised embryo explant. In yet other embodiments the mature embryo explant has a moisture content within a range from about 3% to about 25%. In still other embodiments the mature embryo explant is excised from a plant seed having a moisture content within a range from about 3% to about 25%. In further embodiments the delivering step comprises delivering a DNA molecule or vector comprising the recombinant DNA construct and the second recombinant DNA construct to the mature plant embryo explant.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1A:
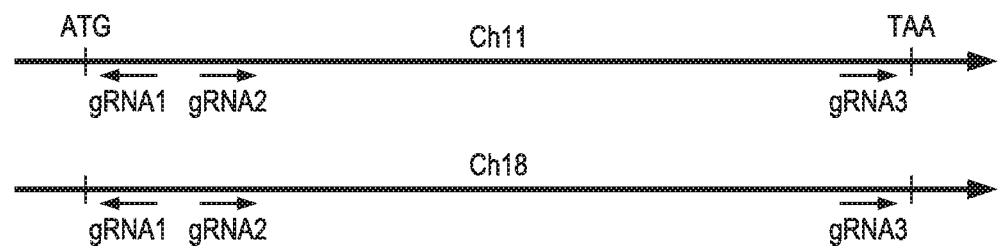
FIG. 1A is a diagram showing the two PDS loci in soybean on chromosomes 11 (Ch11) and 18 (Ch18) with the target site locations for three guide RNAs shown.

Gene function analysis and crop improvement using genome editing technologies have great promise in improving agriculture. While genome editing reagents have been delivered to culturable plant cells in the form of DNA, delivery of DNA encoding genome editing reagents to mature plant embryo explants to regenerate or develop edited plants has not been described. Plant cells and tissues that have been transformed with DNA encoding genome editing reagents can be limited in their regenerative capacity, and many plant germplasms may not be amenable to these culturing methods. Indeed, many crop plants and cultivars are unable to form callus tissue, suspension culture or protoplasts effectively. Thus, existing genome editing methods may be species- and genotype-dependent depending on the type of explant and culturing requirements, and in many cases limited to less commercial germplasms and cultivars of agronomically important crops, which require multiple rounds of backcrossing with more elite donor lines to introgress the genomic edit or site-directed integration into a desirable genetic background.

The present disclosure overcomes deficiencies in the art by providing methods of delivering genome editing reagents into mature or dry excised embryo explants (DEEs) as DNA encoding a genome editing reagent, such as a nuclease protein or guide nucleic acid, which may be delivered via bacterially mediated transformation or coated onto particles for biolistic delivery to explants. A "dry excised explant" is a mature embryo explant taken or excised from a mature dry seed. A plant seed naturally dries during its maturation process. As described further below, other types of explants may be taken or excised from a mature seed depending on their treatment, such as after wetting, imbibing, etc., a dry seed, and an explant may be wetted, imbibed, etc., after being excised from a dry seed. Edits or site-directed integrations may be generated by delivering DNA encoding a genome editing reagent, such as a nuclease protein or guide nucleic acid, to one or more cells of a meristematic tissue, such as an embryonic meristem tissue, without any prior callus formation step. By avoiding the need for a callus phase prior to delivery of a genome editing reagent into one or more cells of the targeted explant according to present methods, the genotype and species dependence with prior methods may be reduced or eliminated, and effective delivery of DNA encoding genome editing reagents, such as a nuclease protein or guide nucleic acid, into those targeted explants may be achieved. Accordingly, the presently disclosed methods for genome editing reagent delivery can be carried out directly into a variety of plant germplasms, including elite germplasm lines of agronomically important crop species, which may allow for direct regeneration of plants of a desired germplasm containing the targeted edit or site-directed integration of an insertion sequence or transgene.

Dry excised explants with a desired edit or site-directed integration of a sequence or transgene may be generated according to genome editing methods of the present disclosure, which may be allowed to develop rather normally into adult $R_0$ plants containing the desired edit or site-directed integration with only minor culturing and/or regeneration steps. Such $R_0$ plants can be developed or regenerated from an explant without the need for embryogenic or callus cultures. The targeted edit or site-directed integration in $R_0$ plants produced by methods of the present disclosure can be further transmitted in the germ line to produce genome-edited $R_1$ seeds and plants as well as subsequent generations of seeds and plants having the desired edit or site-directed integration.

The ability to generate genome edited $R_0$ plants without extensive culturing of the dry excised explants prior to introduction of a genome editing reagent, such as a nuclease protein or guide nucleic acid, allows for methods of the present disclosure to be carried out more rapidly and efficiently, thus enabling the potential for its implementation in large-scale, commercial production of genome edited crop plants. Dry excised explants may be taken from seeds and used almost directly as targets for genome editing or site-directed integration. According to some embodiments, dry excised explants may be taken from mature dry seeds and used as targets for editing with perhaps only minimal wetting, hydration or pre-culturing steps. Accordingly, dry excised explants from storable dry seeds may be conveniently utilized as targets for genome editing or site-directed integration of an insertion sequence or transgene. As an alternative to dry excised explants, "wet" or "dried wet" embryo explants (including for example, primed or germinated embryo explants) may be used as targets for genome editing. Such "wet" embryo explants are dry excised explants that are subjected to wetting, hydration, imbibition or other minimal culturing steps prior to receiving an editing enzyme. Similarly, "wet excised" explants from imbibed or hydrated seeds may also be used as targets. A "wet" embryo explant is hydrated or imbibed after its excision from a seed, whereas a "wet excised" embryo explant is excised from an already hydrated or imbibed seed.

I. Methods of Transformation

Embodiments of the present disclosure provide methods of editing the genome of dry excised explants (DEEs) from dry seeds of a plant, comprising introducing a DNA encoding genome editing reagent, such as a nuclease protein or guide nucleic acid, which may be provided with a donor template, for transformation, such as via biolistic particle-mediated or bacterially mediated (e.g., *Agrobacterium* mediated) delivery, into at least one cell of an explant to produce a genome edit or site-directed integration in at least one cell of the explant. Methods of the present disclosure may be carried out by targeting a dry excised embryo explant from harvested seeds without extensive culturing of the explant prior to delivery of the DNA encoding one or more genome editing reagents. Such explants may be excised from storable, dry seeds, or may be "wet", "dried wet", or "wet excised" embryo explants.

According to some embodiments, dry explants excised from plant seeds may optionally be precultured in an aqueous medium for a limited time prior to delivery of a DNA encoding a genome editing reagent, such as a nuclease protein or guide nucleic acid, to the explant. Such a preculture medium may comprise various salt(s) (e.g., MS basal salts, B5 salts, etc.) and other ingredients, such as various osmoticum(s), sugar(s), antimicrobial agent(s), etc. The preculture medium may be solid or liquid and may further comprise one or more plant growth regulators or phytohormones including an auxin(s), cytokinin(s), etc. According to some embodiments, multiple explants may be precultured together in the same medium or container. For example, a range of 2-100 explants, such as about 25 explants, about 50 explants, about 75 explants, or about 100 explants, may be plated on or in the same preculture medium, although a larger number of explants may be precultured together depending on the type of explant, the size of the container, dish, etc. According to some embodiments, the preculture medium may comprise an auxin, such as 2,4-D, indole acetic acid (IAA), dicamba, 1-naphthaleneacetic acid (NAA), etc., and a cytokinin or similar growth regulator, such as thidiazuron (TDZ), 6-benzylaminopurine (BAP), zeatin or zeatin riboside, etc. Such a preculture or preculturing step may enhance the ability to edit and/or regenerate the explant. The relative amounts of auxin and cytokinin (or similar growth regulator) in the preculture medium may be controlled or predetermined such that editing and/or regeneration success is improved while avoiding callus formation from the explant (even over prolonged time periods). According to some embodiments, the preculture medium may comprise both an auxin, such as 2,4-D, and a cytokinin, such as TDZ. For example, the concentration of cytokinin, such as TDZ, in the preculture medium (if present) may be in a range from zero (0) to about 5 ppm, such as from about 0.3 to about 4 parts per million (ppm), from about 0.5 to about 3 ppm, from about 1 to about 2, or within any other intermediate range of concentrations. In certain aspects, the concentration of cytokinin in the preculture medium may be 0, about 0.1 ppm, about 0.2 ppm, about 0.3 ppm, about 0.4 ppm, about 0.5 ppm, about 0.6 ppm, about 0.7 ppm, about 0.8 ppm, about 0.9 ppm, about 1.0 ppm, about 1.25 ppm, about 1.5 ppm, about 1.75 ppm, about 2 ppm, about 2.5 ppm, about 3 ppm, about 3.5 ppm, about 4 ppm, about 4.5 ppm or about 5 ppm. In the case of TDZ, the concentration may preferably be less than 2 ppm, or in a range from about 0.7 to about 1.3 ppm, or from about 0.5 to about 1 ppm, or about 0.3 ppm or about 1.5 ppm. In certain aspects, the concentration of TDZ is about 0.1 ppm, about 0.2 ppm, about 0.3 ppm, about 0.4 ppm, about 0.5 ppm, about 0.6 ppm, about 0.7 ppm, about 0.8 ppm, about 0.9 ppm, about 1.0 ppm, about 1.1 ppm, about 1.2 ppm, about 1.3 ppm, about 1.4 ppm, about 1.5 ppm, about 1.6 ppm, about 1.7 ppm, about 1.8 ppm or about 1.9 ppm. The concentration of auxin, such as 2,4-D, may be in a range from zero (0) to about 2 ppm, or from about 0.1 ppm to about 1 ppm, or from about 0.1 ppm to about 0.5 ppm, or within any other intermediate range of concentrations. In certain aspects, the concentration of auxin is about 0.1 ppm, about 0.2 ppm, about 0.3 ppm, about 0.4 ppm, about 0.5 ppm, about 0.6 ppm, about 0.7 ppm, about 0.8 ppm, about 0.9 ppm, about 1.0 ppm, about 1.1 ppm, about 1.2 ppm, about 1.3 ppm, about 1.4 ppm, about 1.5 ppm, about 1.6 ppm, about 1.7 ppm, about 1.8 ppm or about 1.9 ppm.

Depending in part on the temperature of the preculture medium and/or explant surroundings, the time period for the preculture step may vary. In general, the time period for the preculture step may also be controlled and limited to within a range from about 1 or 2 hours to about 5 days, such as from about 12 hours to about 60 hours, or from about 12 hours to about 48 hours, or any other range of time periods therein. Limiting the amount of time for the preculture step may also avoid callus formation despite the presence of plant growth regulators. Optimal preculture duration may also improve plant regeneration frequency. During the preculture step, the explants may be kept on the same medium or transferred one or more times to a fresh medium/media. Lighting and/or temperature conditions of the optional preculture step may also be controlled. For example, the explant may be exposed to a 16/8 hour photoperiod exposure during the preculture step, or possibly to various other light and dark cycles or time periods. Alternatively, the preculture step may be carried out in the dark or low light conditions. The temperature of the explant preculture medium and surroundings may also vary from about 18° C. to about 35° C., or from about 25° C. to about 30° C., or about 28° C., and including all intermediate ranges and values.

According to some embodiments, and regardless of whether a preculture step is performed, dry excised explants for transformation may optionally be exposed to a hydration or imbibition medium for a limited time prior to preculture and/or exposure to a genome editing reagent. Such a hydration or hydrating step may make the explants from dry or dried seeds more amenable to editing or site-directed integration. Indeed, the hydration or imbibition step may be performed without a separate preculture step prior to transformation. The hydration medium may consist of only water, or may further comprise one or more known osmoticum(s), such as sugar(s) (e.g., sucrose, etc.), polyethylene glycol (PEG), etc. For example, the hydration medium may include about 10% sucrose and/or about 20% PEG. Without being bound by any theory, the osmoticum may regulate or slow the rate of hydration of the explant. Other ingredients may also be included in the hydration medium, such as various salts, etc. The time period for the hydration step may generally be short, such as from about 2 minutes to about 12 hours, or from about 20 minutes to about 6 hours, or from about 30 minutes to about 2 hours, or for about 1 hour. The hydration or imbibition step may be short enough in time such that germination, or at least any observable germination or developmental changes, of the explant does not occur. Alternatively, an embryo explant may be primed for germination or even allowed to germinate prior to delivery of a genome editing reagent. For example, an embryo explant may be primed for germination by wetting and then drying the explant (to produce a "dried wet" embryo explant) with arrested germination. Furthermore, a "wet excised" embryo (an embryo explant excised from a hydrated or wet seed) may also be used as a target for transformation. Before, during and/or after any of the hydration and/or preculture step(s), various rinse steps may also be performed.

According to some embodiments, a hydration and/or preculture step(s) may be included prior to transformation to improve editing, especially for dry (or dried) explants, such as those taken from mature and/or dry (or dried) seeds, although either or both of these steps may be optional depending on the moisture content and/or type of explant used as a target for editing. However, the hydration and/or preculture steps may be optional and not included or performed, especially when "wet" or "wet excised" embryo explants are used as targets since these explants may already have a sufficient level of hydration or moisture content.

Whether or not the hydration and/or preculture step(s) are performed, the explant may be subjected to transformation with a DNA molecule encoding a genome editing reagent, such as a nuclease protein or guide nucleic acid, which may be coated onto a particle for biolistic delivery or incorporated into a vector (e.g., T-DNA vector) for transformation, to produce an explant having at least one genome-edited cell. Following delivery or transformation of a DNA encoding a genome editing reagent, explants may then be grown, developed, regenerated, etc., into a plant under selection pressure to select for growth and development of the genome-edited cell(s) of the explant. In certain embodiments, a DNA encoding one or more genome editing reagents may be co-transformed or co-delivered with a selectable marker gene, such that survival, growth and development of genome-edited cells may be favored in the presence of a corresponding selection agent. According to some embodiments, a DNA encoding one or more genome editing reagents may be co-transformed or co-delivered a donor template molecule for site directed integration of an insertion sequence or transgene (e.g., gene of interest) into the genome of a plant cell. A donor template molecule for site directed integration may further comprise a selectable marker gene that may be used as a basis for selection. According to some embodiments, a DNA encoding one or more genome editing reagents may be co-transformed or co-delivered with a guide nucleic acid or a DNA encoding a guide nucleic acid. According to some embodiments, a DNA encoding one or more genome editing reagents that is transformed or delivered to an explant may also comprise one or more of: a donor template sequence and/or a selectable marker gene.

According to certain embodiments of the present disclosure, a transformation vector having incorporated, or a particle having on its surface, or coated or applied with, a DNA encoding one or more genome editing reagents is introduced into at least one cell of a target explant via transformation or particle-mediated bombardment of the explant. Such particle-mediated bombardment may utilize any suitable particle gun device known in the art, such as a helium particle gun, electric particle gun, etc. Prior to bombardment, particles may be loaded, applied or coated with copies of the DNA construct or molecule encoding one or more genome editing reagents, and optionally with a guide RNA, marker gene and/or donor template. The DNA construct or molecule encoding one or more genome editing reagents may comprise a sequence encoding a guide RNA, a marker gene, and/or a donor template. The particles themselves may include any suitable type of particle or bead known in the art, such as gold or tungsten beads, etc. Blasting conditions for the particle gun are well-known in the art, and various conventional screens, rupture disks, etc., may be used, such as for a helium particle gun. An electric gun may provide some advantages in reducing the amount of time required for transformation and by using fewer consumables in the process.

For particle bombardment, dry embryo explants may be plated onto a target medium or substrate that is able to hold the explants in place and properly oriented for blasting. Such a target medium or substrate may contain, for example, a gelling agent, such as agar, and carboxymethylcellulose (CMC) to control the viscosity of the medium or substrate. Plating of the explants in a liquid, such as in a hydration, preculture or rinse medium, may facilitate spreading and positioning of the explants. The explants targeted for particle bombardment according to certain embodiments may be positioned such that the meristematic tissue of the explant preferentially receives the particles of the blast. For example, explants may be placed on a surface with their meristems facing upward to preferentially receive the coated particles during bombardment. Each explant may also be blasted with coated particles at various pressures, forces, and/or once or multiple times.

According to embodiments of the present disclosure where a selectable marker gene is co-delivered with a DNA sequence encoding one or more genome editing reagents, the targeted explant may be cultured on (or in) a post-culture selection medium (or a series of selection media) after bombardment or transformation to allow or select for cells and tissues of the explant containing the selectable marker gene to regenerate or develop into a plant or plant part, such as a root and/or shoot. The selectable marker gene may be co-delivered with the DNA sequence encoding one or more genome editing reagents to select for cells that may have expression of the one or more genome editing reagents along with the selectable marker gene. In general, a selection media will contain a selection agent to bias or favor the survival, growth, proliferation and/or development of cells of the explant based on the expression of a selectable marker gene delivered to at least one cell of the explant (the selectable marker gene provides tolerance to the selection agent when expressed in the recipient cell(s) and progeny cells thereof). According to some embodiments, however, the bombarded or transformed explant may not be subjected to selection pressure and developed or regenerated plants may ultimately be screened for the presence of an edit or mutation at the target site.

According to some embodiments, however, explants may optionally be cultured on (or in) a first post-culture resting medium lacking the selection agent for a first period of time immediately following transformation or bombardment of the target explant to allow the explant to recover and/or begin to express the selectable marker gene. Such a resting step may be for a time period in a range from about one hour to about 24 hours, or form about 6 hours to about 18 hours, or from about 10 hours to about 15 hours, (e.g., about 12 hours or overnight). Although recovery of edited plants may be improved by having a non-selective period for recovery (e.g., culturing on a resting medium), the frequency at which edited plants are recovered may decline if selection is initiated too late (e.g., greater than 18-24 hours after bombardment). Each of the post-culture, selection or resting media may include standard plant tissue culture media ingredients, such as salts, sugars, plant growth regulators, etc., and culturing on these media may be carried out at standard or varied temperatures (e.g., 28° C.) and lighting conditions (e.g., a 16/8 hour photoperiod). However, the first post-culture or resting step may be included or omitted prior to selection depending on the editing frequency and selection scheme, such as the particular selectable marker gene and selection agent used.

Following any initial recovery and culturing of the explants on the first non-selective resting medium, the explants may optionally undergo an enhancing step. According to these embodiments, the explants may be exposed to, placed on (or in), etc., a second post-culture or enhancement medium comprising an osmoticum, such as polyethylene glycol (PEG), etc., and/or a calcium-containing salt compound, such as calcium nitrate $[Ca(NO_3)_2]$, etc. For example, the concentration of calcium nitrate may be about 0.1 M, and the concentration of PEG may be about 20%, although their concentrations may vary. This enhancing medium may also lack a selection agent. Exposing the bombarded explants to the enhancement medium may function to further drive the coated particles and/or DNA encoding one or more genome editing reagents and marker gene construct (if used) into the explant cells. The explants may be placed in or on the enhancement medium for only a short time period, such as in a range from about 30 minutes to about 2 hours, or for about 1 hour, which may then be followed by a rinse step(s) prior to any further culturing or selection steps.

As mentioned above, the bombarded or transformed explants may be contacted with one or more selection media containing a selection agent to bias the survival, growth, proliferation and/or development of cells having expression of a selectable marker gene construct used for co-transformation. The selectable marker gene will generally be paired to the selection agent used for selection such that the selectable marker gene confers tolerance to selection with the selection agent. For example, the selectable marker gene may be an adenylyltransferase gene (aadA) conferring tolerance to spectinomycin or streptomycin as the selection agent.

A plant selectable marker gene or transgene may include any gene conferring tolerance to a corresponding selection agent, such that plant cells transformed with the plant selectable marker transgene may tolerate and withstand the selection pressure imposed by the selection agent. As a result, cells of an explant receiving the selectable marker gene are favored to grow, proliferate, develop, etc., under selection. Although a plant selectable marker gene is generally used to confer tolerance to a selection agent, additional screenable marker or reporter gene(s) may also be used. Such screenable marker or reporter genes may include, for example, β-glucuronidase (GUS; e.g., as described, for example, in U.S. Pat. No. 5,599,670) or green fluorescent protein and variants thereof (GFP described, for example, in U.S. Pat. Nos. 5,491,084 and 6,146,826). A variety of screenable markers or reporter genes that are detectable in a plant, plant part or plant cell are known in the art, such as luciferase, other non-GFP fluorescent proteins, and genes conferring a detectable phenotype in a plant, plant part or seed (e.g., phytonene synthase, etc.). Additional examples of screenable markers may include secretable markers, such as opine synthase genes, etc., whose expression causes secretion of a molecule(s) that can be detected as a means for identifying transformed cells.

A plant selectable marker gene may comprise a gene encoding a protein that provides or confers tolerance or resistance to an herbicide, such as glyphosate and glufosinate. Useful plant selectable marker genes are known in the art and may include those encoding proteins that confer resistance or tolerance to streptomycin or spectinomycin (e.g., adenylyltransferase, aadA, or spec/strep), kanamycin (e.g., neomycin phosphotransferase or nptII), hygromycin B (e.g., hygromycin phosphotransferase, hpt, hph or aph IV), gentamycin (e.g., aac3 and aacC4), and chloramphenicol (e.g., chloramphenicol acetyl transferase or CAI). Additional examples of known plant selectable marker genes encoding proteins that confer herbicide resistance or tolerance include, for example, a transcribable DNA molecule encoding 5-enolpyruvylshikimate-3-phosphate (EPSP) synthase (EPSPS for glyphosate tolerance; e.g., as described in U.S. Pat. Nos. 5,627,061; 5,633,435; 6,040,497; and 5,094,945); a transcribable DNA molecule encoding a glyphosate oxidoreductase and a glyphosate-N-acetyl transferase (GOX; e.g., as described in U.S. Pat. No. 5,463,175; GAT described in U.S. Patent Publication No. 2003/0083480); a transcribable DNA molecule encoding phytoene desaturase (crtI; e.g., as described in Misawa, et al., *Plant Journal*, 4:833-840 (1993) and Misawa, et al., *Plant Journal*, 6:481-489 (1994) for norflurazon tolerance); a transcribable DNA molecule encoding dicamba monooxygenase (DMO) gene (e.g., U.S. Patent Application Nos. 2003/0115626 and 2003/0135879; and Behrens et al., *Science* 316(5828):1185 2007) for dicamba tolerance; and a bialaphos resistance (bar) or phosphinothricin N-acetyltransferase (pat) gene (e.g., as described in DeBlock, et al., EMBO Journal, 6:2513-2519 (1987) for glufosinate and bialaphos tolerance.

To undergo the selection step(s), the explants may be contacted with, or placed on (or in), one or more selection media containing a selection agent. In addition to applying the selection pressure, the selection media may simultaneously provide for the regeneration or development of shoots, roots and/or whole plants from the bombarded explants. Alternatively, a regeneration medium may be used for development or regeneration of one or more shoots and/or roots without the presence of a selection agent. The regeneration and/or selection media may contain various standard plant tissue culture ingredients, such as salts (e.g., MS or B5 salts), sugar(s), etc. The regeneration and/or selection media may optionally include plant growth regulator(s), such as an auxin and/or a cytokinin, which may promote or assist with the development, elongation or regeneration of shoots and/or roots (and ultimately whole plants). The regeneration and/or selection step(s) may be carried out within a range of standard or varied temperatures (e.g., 28° C.) and lighting conditions (e.g., 16/8 photoperiods). Such development of a genome-edited $R_0$ plant on the selection media from a bombarded explant may largely resemble a normal process of germination and plant development, although some reorganization of the meristem may occur in response to the selection pressure to form shoots and/or roots and other plant parts of the adult plant. Importantly, not only is a callus phase avoided before the bombardment or transformation step, the explants may further develop or regenerate into a genome-edited $R_0$ plant without forming an embryogenic callus from the explant after transformation.

According to embodiments of the present disclosure, the explants may be cultured in a first selection medium (or a series of selection media) until green shoots are formed, which may then be taken or cut and transferred to a new selection medium. The transferring or subculturing process may be repeated once or several times (e.g., 2, 3, 4, or 5 times) to provide multiple rounds of transfer, subculture and/or selection. It is believed that multiple rounds of transfer, subculture and/or selection of shoots from the explants under selection pressure may expand or increase the number, proportion and/or ubiquity of genome-edited cells throughout the later developed or regenerated genome-edited $R_0$ plant.

According to some embodiments, a regeneration medium, which may also be a selection medium, such as one or more of the selection media described above, may also function as a rooting medium to cause or allow for the formation and development of root(s) from the transferred or subcultured shoot(s), which may comprise one or more plant growth regulator(s), such as an auxin and/or a cytokinin. The rooting medium/media may each also be a selection medium and comprise a selection agent in addition to one or more plant growth regulator(s). Rooted plantlets developed or regenerated from the bombarded explants (through serial transfer or subculture under selection pressure) may eventually be transferred to PlantCon™ or other suitable containers and/or potted soil for the continued development of genome-edited $R_0$ plants, and genome-edited $R_1$ seeds may then be harvested from those genome-edited $R_0$ plants. Only a few rounds of sequential subculturing (and eventual rooting) of green shoots derived from the initially bombarded or transformed explants under selection pressure may be sufficient to form genome-edited $R_0$ plantlets that may be further developed into fertile plants that produce genome-edited $R_1$ plants and seeds. The present disclosure represents a significant advance and improvement in the art by providing for the production of genome-edited plants at a reasonable frequency in different plant germplasms. Indeed, methods of the present disclosure avoid the need for a callus phase at any stage throughout the process of preparing the dry excised explant for bombardment or transformation and then developing or regenerating a genome-edited $R_0$ plant from the bombarded or transformed explant. In contrast to the present disclosure, existing methods for genome-editing have generally been limited to certain explant types and plant germplasms and cultivars that are amenable to more extensive culturing steps.

According to embodiments of the present disclosure, one or more selection step(s) may be performed in a single selection medium or may more preferably be carried out in a series of selection steps or media. The amount or concentration of the selection agent in a selection medium may vary depending on the particular selection agent used. For example, the amount of spectinomycin used for the selectable marker gene aadA may be in a range from about 50 ppm to about 250 ppm, or about 100 ppm or about 150 ppm. According to some embodiments, the amount or concentration of selection agent may remain constant throughout the period for selection, or the amount or concentration of selection agent may be stepped up or increased over the selection period. A stepped approach may allow more time for transformed explant cell(s) to recover until they can achieve a more robust expression of the selectable marker gene to withstand stronger selection pressure. However, expression of the selectable marker gene may be sufficient by the time of initial selection pressure, such that the stepped selection approach would be unnecessary. With either approach, the explant may be periodically transferred or subcultured to fresh selection media, or the selection media may be periodically replaced and refreshed with new selection media. According to some embodiments, the explants may be kept in or on each of the selection media for a time period in a range from about a few days (e.g., 2 or 3 days) to several weeks (e.g., 3-4 weeks), or from about 1 week to about 3 weeks, or for about 2 weeks, before being transferred or subcultured to the next medium. According to specific embodiments involving the use of spectinomycin as the selection agent, the concentration of spectinomycin may be increased in a stepped fashion from about 50 ppm to about 500 ppm, or alternatively, the amount concentration of spectinomycin may be held relatively constant (e.g., at about 100 ppm, about 150 ppm, or about 200 ppm).

According to some embodiments, a DNA encoding one or more genome editing reagents for genome editing may be transformed into at least one cell of a mature embryo explant using any transformation method known in the art. Various methods are known for transferring genes into plant tissues including high velocity microprojection, microinjection, electroporation, direct DNA uptake, and bacterially mediated transformation. According to some embodiments, a DNA encoding one or more genome editing reagents for genome editing may be transformed into at least one cell of a mature embryo explant via bacterially mediated transformation. Bacteria known to mediate plant cell transformation include a number of species of the Rhizobiaceae and Rhizobia families, including, but not limited to, *Agrobacterium* sp., *Sinorhizobium* sp., *Mesorhizobium* sp., and *Bradyrhizobium* sp. (see, e.g., Broothaerts et al., 2005; and U.S. Patent Application Publication Nos. 2007/0271627 and 2008/0280361).

Bacterially mediated delivery of a DNA molecule (e.g., *Agrobacterium*-mediated delivery; see also, e.g., U.S. Pat. Nos. 5,563,055; 5,591,616; 5,693,512; 5,824,877; and 5,981,840) can be made into cells in the living meristem of an embryo excised from a seed, such as soybean and other crop seeds. The meristematic region may be cultured in the presence of a selection agent to regenerate a R0 plant having one or more cells transformed with the DNA molecule. The formation of shoots and/or roots can occur in various culture media to regenerate a plant from one or more explant cells, which may include a transformed meristematic cell.

Possible selection agents may include auxin-like herbicides such as dicamba or 2,4-D, MCPA, glufosinate, acetolactate synthase inhibitors, protoporphyrinogen oxidase inhibitors, and hydroxyphenyl-pyruvate-dioxygenase inhibitors, neomycin, kanamycin, paramomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of selectable marker genes providing resistance against these selection agents are also known in the art.

A variety of tissue culture media are known that, when supplemented appropriately, support plant tissue growth and development, including formation of mature plants from excised meristems or embryos. These tissue culture media can either be purchased as a commercial preparation or custom prepared and modified by those of skill in the art. Examples of such media include, but are not limited to those described by Murashige and Skoog, (1962); Chu et al., (1975); Linsmaier and Skoog, (1965); Uchimiya and Murashige, (1962); Gamborg et al., (1968); Duncan et al., (1985); McCown and Lloyd, (1981); Nitsch and Nitsch, (1969); and Schenk and Hildebrandt, (1972), or derivations of these media supplemented accordingly. Those of skill in the art are aware that media and media supplements such as nutrients and growth regulators for use in transformation and regeneration are usually optimized for the particular target crop or variety of interest. Reagents are commercially available and can be purchased from a number of suppliers (see, for example Sigma Chemical Co., St. Louis, Mo. and Phytotechnology Laboratories, Shawnee Mission, Kans.).

Co-culture and subsequent steps may be performed in dark conditions, or in lighted Percival incubators, for instance for 2 to 5 days with a photoperiod of 16 hours of light, 8 hours of dark. In one embodiment, the light intensity may be, for example, at least about 5 .mu.E, including, at least about 10 .mu.E or 25 .mu.E, including between about 5 uE and about 200 uE or other lighting conditions that allow for normal plastid development at a temperature of approximately 23 to 25.degree. C., and may be performed at up to about 35.degree. C.

The methods of the present disclosure allow for regeneration and/or development of candidate genome-edited plants from one or more bombarded or transformed explants without the need for extensive culturing, thus increasing the efficiency in identifying and growing shoots and plants comprising one or more genome edited cells and reducing costs and labor necessary to produce genome-edited plants of a desired variety or germplasm. For instance, after putative transformants have been identified using selectable markers, plantlets may be placed in soil or on a soil substitute, such as on a rooting medium, in the presence or absence of the selection agent. Shoots elongating from selected or regenerated explants may be assayed for the presence of a genome edit at a target site using molecular techniques. Genome-edited $R_0$ plants can further give rise to genome-edited $R_1$ plants and seeds that can produce subsequent progeny plants and seeds that are also genome-edited. Although genome-edited $R_0$ plants may be produced by methods of the present disclosure with little or no selection pressure, maintaining selection with the appropriate selection agent may be maintained over one or more culturing or regenerating steps. R1 plants determined to have one or more genome edits at a desired target site may be crossed with another plant, and homozygous genome-edited plants may be selected in a subsequent generation having the mutation(s) or edit(s) fixed with respect to inheritance of the genome edit(s) or mutation(s) in subsequent generations (without segregation of the edit(s) or mutation(s) in progeny plants and with stable maintenance of homozygosity in progeny with self-crossing). As described above, the growth, survival, development, etc., of genome-edited cells in the $R_0$ plant may also be selectively or preferentially achieved or favored by exerting a selection pressure with a selection agent during culturing, sub-culturing, shoot elongation and/or rooting step(s) of the explant to produce a $R_0$ plant having a greater proportion of its cells having a genome edit(s) or mutation(s) due to co-delivery of a selectable marker gene, although selection pressure may alternatively be continued (e.g., periodically, etc.) after initial culturing and/or during the remaining life of the $R_0$ plant (e.g., as a topical spray, soil or seed application, etc.).

A variety of tissue culture media are known that, when supplemented appropriately, support plant tissue growth and development, including formation of mature plants from excised plant tissue. These tissue culture media can either be purchased as a commercial preparation or custom prepared and modified by those of skill in the art. Examples of such media include, but are not limited to those described by Murashige and Skoog, *Physiol. Plant* 15:473-497, 1962); Chu et al., (*Scientia Sinica* 18:659-668, 1975); Linsmaier and Skoog, (*Physiol. Plant* 18:100-127, 1965); Uchimiya and Murashige, *Plant Physiol.* 57:424-429, 1976; Gamborg et al., *Exp. Cell Res.* 50:151-158, 1968; Duncan et al., *Planta* 165:322-332, 1985; McCown and Lloyd, HortScience 16:453, 1981; Nitsch and Nitsch *Plant Physiol.* 44:1747-1748, 1969; and Schenk and Hildebrandt, *Can. J. Bot.* 50:199-204, 1972, or derivations of these media supplemented accordingly. Those of skill in the art are aware that media and media supplements, such as nutrients and plant growth regulators for use in transformation, selection and regeneration are usually optimized for the particular target crop or variety of interest. Tissue culture media may be supplemented with carbohydrates such as, but not limited to, glucose, sucrose, maltose, mannose, fructose, lactose, galactose, and/or dextrose, or ratios of carbohydrates. Reagents are commercially available and can be purchased from a number of suppliers (see, for example Sigma Chemical Co., St. Louis, MO; and PhytoTechnology Laboratories, Shawnee Mission, KS). These tissue culture media may be used as a resting media or as a selection media with the further addition of a selection agent, and/or as a regeneration media if supplemented with one or more plant growth regulators.

Embodiments of the present disclosure also provide genome-edited plants, plant parts and seeds produced by the transformation methods of the present disclosure that comprise one or more edit(s) or mutation(s) at or near a target site. Plant parts, without limitation, include fruit, seed, endosperm, ovule, pollen, leaf, stem, and roots. In certain embodiments of the present disclosure, the plant or plant part is a seed.

II. Transformable Explants

Methods of the present disclosure may further comprise step(s) for excising, or excision of, at least a portion of a plant embryo from a plant seed by any suitable manual or automated method prior to transformation. According to embodiments of the present disclosure, suitable embryo explants further comprise a meristem or meristematic tissue of the embryo, or at least a portion of the meristem, or at least one meristematic cell of the embryo explant, since targeting of the meristematic cells of an explant for transformation for delivery of a DNA encoding one or more genome editing reagents, which may improve or be necessary for effective creation and development or regeneration of a genome-edited plant. An embryo explant may lack one or more embryonic tissues, such as cotyledon(s), hypocotyl(s), radicle, etc., as long as it retains at least a portion of the embryo meristem. Use of mature embryo explants excised from dry seeds may be preferred according to many embodiments of the present disclosure, although they may require hydration and/or preculture step(s) prior to transformation.

Any suitable method for producing or excising embryo explants from plant seeds may be used in conjunction with embodiments of the present disclosure. These methods may be automated and/or performed manually and may involve a singulated or bulk process. According to many embodiments, the embryo explant may be a mature embryo explant (or portion thereof) taken or excised from a dry mature plant seed. For any given species of plant, a mature seed or embryo may be defined in terms of being greater than or equal to a certain number of days after pollination (DAP) to distinguish an immature seed or embryo of the same species of plant, although the transition from an immature to a mature embryo for a given plant species may be gradual. In general, the transition from immature to mature embryo is accompanied by a natural process of drying or dehydration of the seed and embryo (in addition to other developmental changes) as known in the art.

Since development or maturation of a seed and embryo is accompanied by drying, a mature seed or embryo explant used in methods of the present disclosure may also be defined in terms of its moisture content. Furthermore, an embryo explant may be defined in terms of the moisture content of the seed from which it is excised. For example, a seed or embryo explant used according to present methods may initially have a moisture content at or within a range from about 3% to about 25%, or from about 4% to about 25%, or from about 3% or 4% to about 20%, or at or within any percentage value or range within such broader percentage ranges, depending on the particular species of plant, such as from about 5% to about 20%, about 5% to about 15%, about 8% to about 15% and about 8% to about 13%. Indeed, a plant seed may be artificially dried or dehydrated prior to excision of an embryo explant prior to use in method embodiments of the present disclosure as long as the seed and embryo remain viable and competent for transformation and development or regeneration of plants. Drying of a seed may facilitate excision and/or storage of an embryo explant from the seed. Alternatively, or additionally, a seed may be hydrated or imbibed prior to excision of an explant, such as to facilitate, soften, reduce damage to, and/or maintain viability of the embryo during the excision step. However, hydration of a seed or explant may reduce or eliminate the storability of the seed or explant, even if the seed or explant is subsequently dried or dehydrated.

For a further description of embryo explants and methods for excising embryo explants from dry, dried, and/or mature seeds, which may be previously hydrated, primed or germinated, see, e.g., U.S. Pat. Nos. 8,466,345, 8,362,317, and 8,044,260, and U.S. Patent Publication No. 2016/0264983. Regardless of the type of seeds used and the precise method for mechanically excising embryo explants from the seeds, additional steps and processes, such as sterilization, culling, etc., may also be performed to prepare and/or enrich the explants used for particle bombardment. Dry or dried embryo explants may also be hydrated, primed, and/or germinated after their excision but prior to the transformation step.

Embryonic explants used with the present disclosure may have been removed from seeds less than a day prior to use in present methods, such as from about 1 to 24 hours prior to use, including about 2, 6, 12, 18 or 22 hours before use. According to other embodiments, however, seeds and/or explants may be stored for longer periods, including days, weeks, months or even years prior to their use, depending upon storage conditions used to maintain seed and/or explant viability. An advantage and benefit of using dry mature seeds as a source for producing or excising embryo explants suitable for genome editing is that the dry mature seeds and/or explants may be storable (not germinating and remaining viable and competent for transformation during storage) under dry conditions. Such dry storage conditions may be defined as being stored in an environment or surroundings having a sufficiently low moisture level or humidity, such that the stored seeds and/or explants do not germinate and remain viable and competent for transformation for a desired length of time prior to use in present transformation methods, such as from about 1 hour to about 2 years, or from about 24 hours to about 1 year, or for any particular period of time or range of time periods within those broader ranges of time. By using a storable seed or explant, a reliable supply of seed or explant source material may be available without the need for donor plants. The ability to store mature dry seed relates to a natural property of dry mature seeds and embryos. In other words, a dry mature seed and/or embryo explant may also be defined in terms of its quiescence, stasis or low metabolic state or activity. Thus, the dry seed or explant used according to methods of the present disclosure may be defined in terms of its low metabolic state and/or by its state of metabolic or developmental quiescence or stasis until later hydration and germination of the seed or embryo.

According to some embodiments, hydration or germination of an embryo explant or seed may be performed either before or after excision of the embryo explant from a seed. In other words, apart from any preculturing step, a seed may be imbibed or hydrated to allow the seed to begin germination and/or development prior to excision of the embryo explant, or a dry embryo explant may alternatively be excised from a seed and then imbibed or hydrated to trigger germination and/or development of the embryo explant. The primed or germinated seed may then be subjected to transformation without prior greening of the target tissue, which may be controlled by the amount of time and/or limited exposure to light prior to the particle bombardment step. However, as described above, a hydration step may instead be used only to hydrate a dry embryo explant to make the "wetted" explant more amenable to particle bombardment and delivery of the DNA encoding one or more genome editing reagents without germination or further development of the embryo (e.g., the hydration or imbibition step may be limited in time such that noticeable developmental changes and/or germination of an embryo explant does not occur prior to bombardment).

Explants for use with the method embodiments provided herein may include explants from a wide variety of monocotyledonous (monocot) plants and dicotyledonous (dicot) plants including agricultural crop species, such as maize, wheat, rice, sorghum, oats, barley, sugar cane, African oil palm, switchgrass plant, cotton, canola, sugar beets, alfalfa, soybean, and other Fabaceae or leguminous plants.

III. Genome Editing

The cells, plants, plant parts and seeds of the present disclosure are produced through genome modification using site-specific integration or genome editing. Targeted modification of a plant genome through genome editing can be used to create crop plants having improved traits. Genome editing can be used to make one or more edit(s) or mutation(s) at a desired target site in the genome of a plant, such as to change expression and/or activity of one or more genes, or to integrate an insertion sequence or transgene at a desired location in a plant genome. As used herein, "site-directed integration" refers to genome editing methods and techniques that enable targeted integration or insertion of a polynucleotide (e.g., an insertion sequence, regulatory element or transgene) into a plant genome. As provided herein, a DNA molecule encoding one or more genome editing reagents, may be delivered to a recipient cell of an explant, such as a meristematic cell of the explant. A guide nucleic acid and/or DNA encoding one or more genome editing reagents may be delivered to a recipient cell of an explant via a transformation method without integrating or incorporating a polynucleotide or transgene into the genome of a recipient cell. The DNA molecule encoding one or more genome editing reagents may further comprise (i) a transcribable DNA sequence encoding a guide nucleic acid for an guided nuclease, (ii) a marker gene or transgene, such as a selectable or screenable marker gene, and/or (iii) a donor template.

According to many embodiments, a recombinant DNA construct or molecule is provided comprising a sequence encoding one or more genome editing reagents, wherein the sequence is operably linked to a promoter. The promoter may be heterologous with respect to the sequence encoding the site-specific nuclease. The promoter may be a plant-expressible promoter, such as a constitutive promoter, a tissue-specific or tissue-preferred promoter, a developmental stage promoter, or an inducible promoter. According to some embodiments, the recombinant DNA construct or molecule may further comprise (i) a second sequence or transcribable DNA sequence encoding a guide nucleic acid, wherein the second sequence is operably linked to a second promoter, and/or (ii) a marker gene or transgene, which may be a selectable or screenable marker gene. The second promoter may be heterologous with respect to the sequence encoding the guide nucleic acid. The second promoter may be a plant-expressible promoter, such as a constitutive promoter, a tissue-specific or tissue-preferred promoter, a developmental stage promoter, or an inducible promoter. A marker gene or transgene may comprise a coding sequence operably linked to a promoter, such as a heterologous and/or plant-expressible promoter. According to some embodiments, the recombinant DNA construct or molecule may further comprise a donor template region. Recombinant DNA constructs of the present disclosure may be delivered to a recipient explant cell via any transformation method known in the art, such as particle bombardment or bacterially mediated transformation.

According to many embodiments, a recombinant DNA construct or molecule comprising a sequence encoding one or more genome editing reagents, wherein the sequence is operably linked to a promoter, is applied to, or coated on, a particle or bead for biolistic delivery or incorporated into a transformation vector for transformation into an explant or explant cell or tissue. The promoter may be a heterologous with respect to the sequence encoding the genome editing reagent. The promoter may be a plant-expressible promoter, such as a constitutive promoter, a tissue-specific or tissue-preferred promoter, a developmental stage promoter, or an inducible promoter. According to some embodiments, the recombinant DNA construct or molecule may further comprise a second sequence or transcribable DNA sequence encoding a guide nucleic acid, wherein the second sequence is operably linked to a second promoter. The second promoter may be a heterologous with respect to the sequence encoding the guide nucleic acid. The second promoter may be a plant-expressible promoter, such as a constitutive promoter, a tissue-specific or tissue-preferred promoter, a developmental stage promoter, or an inducible promoter. According to some embodiments, a recombinant DNA construct or molecule comprising a sequence encoding one or more genome editing reagents, wherein the sequence is operably linked to a promoter, and one or more of a guide nucleic acid, a marker gene, and/or a donor DNA template, are applied to, or coated on, a particle or bead for biolistic delivery to an explant or explant cell or tissue.

A DNA construct or molecule encoding any suitable genome editing reagent, such as a zinc-finger nuclease (ZFN), an guided nuclease, a TALE-endonuclease (TALEN), a meganuclease, a recombinase, a transposase, or any combination thereof, may be delivered to a cell of an explant according to the methods provided herein to cause genome editing or site-directed integration at a target site within the genome of the explant cell and/or a progeny cell thereof. In the case of a guided nuclease, such as a Clustered Regularly Interspersed Short Palindromic Repeat (CRISPR) enzyme, the DNA construct or molecule may be co-delivered with a guide nucleic acid to direct the guided nuclease to the target site. A guided nuclease may also include a homolog or modified version of any known guided nuclease sharing conserved amino acids and having a higher percent identity in terms of their respective protein sequences (e.g., at least 90% identity, at least 95% identity, at least 96% identity, at least 97% identity, at least 98% identity, or at least 99% identity in their protein sequences over their alignment length).

According to some embodiments, a DNA construct or molecule encoding a genome editing reagent may be co-delivered with a donor template molecule to serve as a template for making a desired edit, mutation or insertion into the genome at the desired target site through repair of the double strand break (DSB) or nick created by the genome editing reagent. According to some embodiments, a DNA construct or molecule encoding a genome editing reagent may be co-delivered with a DNA molecule comprising a selectable or screenable marker gene. In each case, the DNA construct or molecule encoding a genome editing reagent, optionally in addition to one or more of a guide nucleic acid, a donor template molecule, and/or a DNA molecule encoding a selectable or screenable marker, may be applied to, or coated on, particles used for biolistic or particle delivery to recipient cells of the explant. According to some embodiments, a DNA construct or molecule encoding a genome editing reagent may be applied to, or coated on, particles used for biolistic or particle delivery or incorporated into a vector for transformation into one or more recipient cells of an explant, wherein the one or more recipient cells of the explant comprise one or more DNA molecule(s) and/or transgene(s) prior to particle bombardment or transformation, which may be stably transformed into the genome of the recipient cells, wherein such DNA molecule(s) and/or transgene(s) comprise or encode one or more of the following: (i) a donor template molecule to serve as a template for making a desired edit, mutation or insertion into the genome at the desired target site, (ii) a selectable or screenable marker gene, and/or (iii) a guide nucleic acid to direct a guided nuclease to the desired target site.

A genome editing reagent may be a guided nuclease, which may function as a ribonucleoprotein (RNP) complex with a guide RNA. According to some embodiments, an guided nuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, CasZ, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), and homologs or modified versions thereof). According to some embodiments, a guided nuclease is a Cas9 or Cpf1 enzyme. The DNA construct or molecule encoding a guided nuclease may be delivered with or without a guide nucleic acid.

For guided nucleases, a guide nucleic acid molecule may be further provided to direct the guided nuclease to a target site in the genome of the plant via base-pairing or hybridization to cause a DSB or nick at or near the target site. The guide nucleic acid may be transformed or introduced into a plant cell or tissue as a guide nucleic acid molecule, or as a recombinant DNA molecule, construct or vector comprising a transcribable DNA sequence encoding the guide nucleic acid operably linked to a promoter or plant-expressible promoter. The promoter may be a constitutive promoter, a tissue-specific or tissue-preferred promoter, a developmental stage promoter, or an inducible promoter.

As used herein, the term "guide nucleic acid" refers to a nucleic acid comprising: a first segment comprising a nucleotide sequence that is complementary to a sequence in a target nucleic acid and a second segment that interacts with a guided nuclease protein. In some embodiments, the first segment of a guide comprising a nucleotide sequence that is complementary to a sequence in a target nucleic acid corresponds to a CRISPR RNA (crRNA or crRNA repeat). In some embodiments, the second segment of a guide comprising a nucleic acid sequence that interacts with a guided nuclease protein corresponds to a trans-acting CRISPR RNA (tracrRNA). In some embodiments, the guide nucleic acid comprises two separate nucleic acid molecules (a polynucleotide that is complementary to a sequence in a target nucleic acid and a polynucleotide that interacts with a guided nuclease protein) that hybridize with one another and is referred to herein as a "double-guide" or a "two-molecule guide". In some embodiments, the double-guide may comprise DNA, RNA or a combination of DNA and RNA. In other embodiments, the guide nucleic acid is a single polynucleotide and is referred to herein as a "single-molecule guide" or a "single-guide". In some embodiments, the single-guide may comprise DNA, RNA or a combination of DNA and RNA. The term "guide nucleic acid" is inclusive, referring both to double-molecule guides and to single-molecule guides.

A protospacer-adjacent motif (PAM) may be present in the genome immediately adjacent and upstream to the 5' end of the genomic target site sequence complementary to the targeting sequence of the guide RNA—, immediately downstream (3') to the sense (+) strand of the genomic target site (relative to the targeting sequence of the guide RNA) as known in the art. See, e.g., Wu, X. et al., "Target specificity of the CRISPR-Cas9 system," *Quant Biol.* 2(2): 59-70 (2014). The genomic PAM sequence on the sense (+) strand adjacent to the target site (relative to the targeting sequence of the guide RNA) may comprise 5'-NGG-3'. However, the corresponding sequence of the guide nucleic acid (immediately downstream (3') to the targeting sequence of the guide RNA) may generally not be complementary to the genomic PAM sequence.

The guide nucleic acid may typically be a non-coding RNA molecule that does not encode a protein. The targeter sequence of the guide nucleic acid may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The targeter sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

In addition to the targeter sequence, a guide nucleic acid may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide nucleic acids for genome editing and site-directed integration at a target site within the genome of a plant using a guided nuclease are known in the art.

Several site-specific nucleases, such as recombinases, zinc finger nucleases (ZFNs), meganucleases, and TALENs, are not nucleic acid-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-nucleic acid-guided site-specific nucleases, such as recombinases, zinc finger nucleases (ZFNs), meganucleases, and TALENs, may be designed, engineered and constructed according to known methods to target and bind to a target site at or near the genomic locus of an endogenous gene of a plant to create a DSB or nick at such genomic locus to knockout or knockdown expression of the gene via repair of the DSB or nick, which may lead to the creation of a mutation or insertion of a sequence at the site of the DSB or nick, through cellular repair mechanisms, which may be guided by a donor template molecule.

In some embodiments, a site-specific nuclease is a recombinase. A recombinase may be a serine recombinase attached to a DNA recognition motif, a tyrosine recombinase attached to a DNA recognition motif, or other recombinase enzyme known in the art. A recombinase or transposase may be a DNA transposase or recombinase attached or fused to a DNA binding domain. Non-limiting examples of recombinases include a tyrosine recombinase attached, etc., to a DNA recognition motif provided herein is selected from the group consisting of a Cre recombinase, a Gin recombinase, a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

A site-specific nuclease may be a zinc finger nuclease (ZFN). ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities.

Methods and rules for designing ZFNs for targeting and binding to specific target sequences are known in the art. See, e.g., US Patent App. Nos. 2005/0064474, 2009/0117617, and 2012/0142062. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site. Without being limited by any theory, because the DNA-binding specificities of zinc finger domains can be re-engineered using one of various methods, customized ZFNs can theoretically be constructed to target nearly any target sequence (e.g., at or near a gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick.

A site-specific nuclease may be a TALEN enzyme. TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN also refers to one or both members of a pair of TALENs that work together to cleave DNA at the same site.

Transcription activator-like effectors (TALEs) can be engineered to bind practically any DNA sequence, such as at or near the genomic locus of a gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNAWorks can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011) 39:e82; and tale-nt.cac.cornelledu/about. In another aspect, a TALEN provided herein is capable of generating a targeted DSB.

A site-specific nuclease may be a meganuclease. Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a gene. In another aspect, a meganuclease provided herein is capable of generating a targeted DSB.

According to some embodiments, a donor template may be co-delivered with a DNA construct or molecule encoding a genome editing reagent to a recipient cell of an explant to serve as a template for generating a desired edit during repair of a double-stranded break (DSB) or nick at the target site of the recipient cell genome by the genome editing reagent. Alternatively, a donor template may already be present in a recipient cell of an explant. Similarly, for a guided nuclease, a transcribable DNA sequence or transgene encoding a guide nucleic acid may also be co-delivered with the DNA construct or molecule encoding a guided nuclease to a recipient cell of an explant to serve as a guide to direct the guided nuclease to make a double-stranded break (DSB) or nick at the desired locus or target site in the recipient cell genome. Alternatively, a guide nucleic acid, and/or a DNA molecule or transgene comprising a transcribable DNA sequence encoding a guide nucleic acid, may already be present and/or expressed by a recipient cell of an explant.

According to some embodiments, (i) a DNA construct or molecule encoding a genome editing reagent, a guide nucleic acid, and a donor template may be applied to, or coated on, particles for biolistic delivery to a recipient cell, or (ii) a DNA construct or molecule encoding a genome editing reagent and/or a guide RNA may be applied to, or coated on, particles for biolistic delivery to a recipient cell, and a donor template may optionally be present or expressed in the recipient cell, or (iii) a DNA construct or molecule encoding a genome editing reagent and/or a donor template may be applied to, or coated on, particles for biolistic delivery to a recipient cell, and a guide nucleic acid may be optionally present or expressed in the recipient cell, or (iv) a guide nucleic acid and/or a donor template may be applied to, or coated on, particles for biolistic delivery to a recipient cell, and a genome editing reagent or a DNA construct or molecule encoding a genome editing reagent may be present or expressed in the recipient cell, in each case (i), (ii), (iii) or (iv) to make a double-stranded break (DSB) or nick at the desired locus or target site in the recipient cell genome by the genome editing reagent to create to a templated or non-templated edit or mutation at the desired location in the genome of the recipient plant cell.

Any site or locus within the genome of a plant may potentially be chosen for making a genomic edit (or gene edit) or site-directed integration of a transgene, construct or transcribable DNA sequence. For genome editing and site-directed integration, a double-strand break (DSB) or nick may first be made at a selected genomic locus with a genome editing reagent, such as, for example, a zinc-finger nuclease (ZFN), an engineered or native meganuclease, a TALE-endonuclease, or a guided endonuclease (e.g., Cas9 or Cpf1). Any method known in the art for site-directed integration may be used. In the presence of a donor template molecule with an insertion sequence, the DSB or nick can be repaired by homologous recombination between homology arm(s) of the donor template and the plant genome, or by non-homologous end joining (NHEJ), resulting in site-directed integration of the insertion sequence into the plant genome to create the targeted insertion event at the site of the DSB or nick. Thus, site-specific insertion or integration of a transgene, transcribable DNA sequence, construct or sequence may be achieved if the transgene, transcribable DNA sequence, construct or sequence is located in the insertion sequence of the donor template.

The introduction of a DSB or nick may also be used to introduce targeted mutations in the genome of a plant. According to this approach, mutations, such as deletions, insertions, inversions and/or substitutions may be introduced at a target site via imperfect repair of the DSB or nick to produce a knock-out or knock-down of a gene. Such mutations may be generated by imperfect repair of the targeted locus even without the use of a donor template molecule. A "knock-out" of a gene may be achieved by inducing a DSB or nick at or near the endogenous locus of the gene that results in non-expression of the protein or expression of a non-functional protein, whereas a "knock-down" of a gene may be achieved in a similar manner by inducing a DSB or nick at or near the endogenous locus of the gene that is repaired imperfectly at a site that does not affect the coding sequence of the gene in a manner that would eliminate the function of the encoded protein. For example, the site of the DSB or nick within the endogenous locus may be in the upstream or 5' region of the gene (e.g., a promoter and/or enhancer sequence) to affect or reduce its level of expression. Similarly, such targeted knock-out or knock-down mutations of a gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a gene may be achieved by substituting, inserting, deleting or inverting at least a portion of the gene, such as by introducing a frame shift or premature stop codon into the coding sequence of the gene. A deletion of a portion of a gene may also be introduced by generating DSBs or nicks at two target sites and causing a deletion of the intervening target region flanked by the target sites.

As used herein, a "donor molecule", "donor template", or "donor template molecule" (collectively a "donor template"), which may be a recombinant polynucleotide, DNA or RNA donor template or sequence, is defined as a nucleic acid molecule having a homologous nucleic acid template or sequence (e.g., homology sequence) and/or an insertion sequence for site-directed, targeted insertion or recombination into the genome of a plant cell via repair of a nick or double-stranded DNA break in the genome of a plant cell. A donor template may be a separate DNA molecule comprising one or more homologous sequence(s) and/or an insertion sequence for targeted integration, or a donor template may be a sequence portion (a donor template region) of a DNA molecule further comprising one or more other expression cassettes, genes/transgenes, and/or transcribable DNA sequences. For example, a "donor template" may be used for site-directed integration of a transgene or suppression construct, or as a template to introduce a mutation, such as an insertion, deletion, substitution, etc., into a target site within the genome of a plant. A targeted genome editing technique provided herein may comprise the use of one or more, two or more, three or more, four or more, or five or more donor molecules or templates. A "donor template" may be a single-stranded or double-stranded DNA or RNA molecule or plasmid. An "insertion sequence" of a donor template is a sequence designed for targeted insertion into the genome of a plant cell, which may be of any suitable length. For example, the insertion sequence of a donor template may be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length. A donor template may also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template.

According to some embodiments, a donor template may comprise a "donor template region" of a recombinant polynucleotide molecule or construct that functions as a donor template for site-specific integration of an insertion sequence or template-mediated repair, wherein the recombinant polynucleotide molecule or construct further comprises other elements outside of the donor template region that may be independent of the donor template. For example, a recombinant polynucleotide molecule or construct may comprise a "donor template region" and one or more transgene(s), such as a selectable marker and/or a transcribable DNA sequence encoding a non-coding RNA molecule, such as a guide RNA or a RNA molecule for suppression of a target gene.

An insertion sequence of a donor template may comprise one or more genes or sequences that each encode a transcribed non-coding RNA or mRNA sequence and/or a translated protein sequence. A transcribed sequence or gene of a donor template may encode a protein or a non-coding RNA molecule. A non-coding RNA molecule may be, for example, a guide RNA or a RNA molecule (e.g., a micro RNA (miRNA), small interfering RNA (siRNA), antisense RNA strand, inverted repeat, etc.) targeting a gene for suppression. An insertion sequence of a donor template may comprise a polynucleotide sequence that does not comprise a functional gene or an entire gene sequence (e.g., the donor template may simply comprise regulatory sequences, such as a promoter sequence, or only a portion of a gene or coding sequence) or may not contain any identifiable gene expression elements or any actively transcribed gene sequence. Further, the donor template may be linear or circular, and may be single-stranded or double-stranded. A donor template may be delivered to a cell as a DNA molecule or a RNA molecule expressed from a transgene. A donor template may be delivered to the cell as a naked nucleic acid molecule, or as a complex with one or more delivery agents (e.g., liposomes, proteins, poloxamers, T-strand encapsulated with proteins, etc.). An insertion sequence of a donor template provided herein may comprise a transcribable DNA sequence that may be transcribed into a RNA molecule, which may be non-coding or protein coding, and the transcribable DNA sequence may be operably linked to a promoter and/or other regulatory sequence, such as a constitutive, inducible or tissue-specific promoter.

According to some embodiments, a donor template may not comprise an insertion sequence, and instead comprise one or more homology sequences that include(s) one or more mutations, such as an insertion, deletion, substitution, etc., relative to the genomic sequence at a target site within the genome of a plant, such as at or near a gene within the genome of a plant. Alternatively, a donor template may comprise an insertion sequence that does not comprise a coding or transcribable DNA sequence, wherein the insertion sequence is used to introduce one or more mutations into a target site within the genome of a plant, such as at or near a gene within the genome of a plant.

A donor template provided herein may comprise at least one, at least two, at least three, at least four, at least five, at least six, at least seven, at least eight, at least nine, or at least ten gene(s) or transgene(s) and/or transcribable DNA sequence(s). Alternatively, a donor template may comprise no genes, transgenes or transcribable DNA sequences. Without being limiting, a gene/transgene or transcribable DNA sequence of a donor template may include, for example, an insecticidal resistance gene, an herbicide tolerance gene, a nitrogen use efficiency gene, a water use efficiency gene, a yield enhancing gene, a nutritional quality gene, a DNA binding gene, a selectable marker gene, an RNAi or suppression construct, a genome editing reagent, a single guide RNA of a CRISPR/Cas9 system, a geminivirus-based expression cassette, or a plant viral expression vector system. According to other embodiments, an insertion sequence of a donor template may comprise a protein encoding sequence or a transcribable DNA sequence that encodes a non-coding RNA molecule, which may target an endogenous gene for suppression. A donor template may comprise a promoter operably linked to a coding sequence, gene or transcribable DNA sequence, such as a constitutive promoter, a tissue-specific or tissue-preferred promoter, a developmental stage promoter, or an inducible promoter. A donor template may comprise a leader, enhancer, promoter, transcriptional start site, 5'-UTR, one or more exon(s), one or more intron(s), transcriptional termination site, region or sequence, 3'-UTR, and/or polyadenylation signal, which may each be operably linked to a coding sequence, gene (or transgene) or transcribable DNA sequence encoding a non-coding RNA, a guide nucleic acid, an mRNA and/or protein.

According to present embodiments, a portion of a recombinant donor template polynucleotide molecule (an insertion sequence) may be inserted or integrated at a desired site or locus within the plant genome through genome editing. The insertion sequence of the donor template may comprise a transgene or construct, such as a protein-encoding transgene or transcribable DNA sequence encoding a non-coding RNA molecule that targets an endogenous gene for suppression. The donor template may also have one or two homology arms flanking the insertion sequence to promote the targeted insertion event through homologous recombination and/or homology-directed repair. Each homology arm may be at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence within the genome of a plant cell. According to some embodiments, a recombinant DNA donor template molecule for site-directed or targeted integration of its insertion sequence, and/or recombination of its homologous sequence(s), into the genome of a plant, which insertion sequence may comprise a transgene or construct, such as a transgene or transcribable DNA sequence encoding a non-coding RNA molecule that targets an endogenous gene for suppression, may be co-delivered with a DNA construct or molecule encoding a genome editing reagent. The recombinant DNA donor template may also comprise a selectable or screenable marker gene and/or a transgene encoding a guide nucleic acid, wherein the marker gene and transgene encoding a guide nucleic acid may each be operably linked to a plant-expressible promoter and/or other expression regulatory elements.

As used herein, a "target site" for genome editing or site-directed integration refers to the location of a polynucleotide sequence within a plant genome that is bound and cleaved by a genome editing reagent to introduce a double stranded break, single-stranded nick, or other modification (such as deamination) into the nucleic acid backbone of the polynucleotide sequence and/or its complementary DNA strand within the plant genome. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A "target site" for a guided nuclease may comprise the sequence of either complementary strand of a double-stranded nucleic acid (DNA) molecule or chromosome at the target site. A site-specific nuclease may bind to a target site, such as via a non-coding guide nucleic acid (e.g., without being limiting, a CRISPR RNA (crRNA) or a single-guide RNA (sgRNA) as described further herein). A targeter sequence of a guide nucleic acid provided herein may be complementary to a target site (e.g., complementary to either strand of a double-stranded nucleic acid molecule or chromosome at the target site). It will be appreciated that perfect identity or complementarity may not be required for a targeter sequence of a guide nucleic acid to bind or hybridize to a target site. For example, at least 1, at least 2, at least 3, at least 4, at least 5, at least 6, at least 7, or at least 8 mismatches (or more) between a target site and a targeter sequence of a guide nucleic acid may be tolerated. A "target site" also refers to the location of a polynucleotide sequence within a plant genome that is bound and cleaved by any other genome editing reagent that may not be guided by a guide nucleic acid molecule, such as a meganuclease, zinc finger nuclease (ZFN), a transcription activator-like effector nuclease (TALEN), etc., to introduce a double stranded break, single-stranded nick, or other modification into the polynucleotide sequence and/or its complementary DNA strand.

As used herein, a "target region" or a "targeted region" refers to a polynucleotide sequence or region that is flanked by two or more target sites. Without being limiting, in some embodiments a target region may be subjected to a mutation, base modification, deletion, insertion or inversion following repair of a double-stranded break or nick at the two target sites. As used herein, "flanked" when used to describe a target region of a polynucleotide sequence or molecule, refers to two or more target sites of the polynucleotide sequence or molecule surrounding the target region, with one target site on each side of the target region.

Provided herein are methods for making transgenic or genome edited plants, plant parts and seeds via delivery of a DNA construct or molecule encoding a genome editing reagent into at least one cell of a mature and/or dry excised explant, along with various culturing and treatment steps described herein to develop or regenerate a genome edited or transgenic plant. Further provided are transgenic or genome edited plants, plant parts and seeds made according to the present methods. According to an aspect of the present disclosure, a plant developed or regenerated from an explant subjected to particle bombardment or transformation with a DNA construct or molecule encoding a genome editing reagent, or a progeny plant thereof, can be screened or selected based on a marker, trait or phenotype produced by the edit or mutation, or by the site-directed integration of an insertion sequence, transgene, etc., in the developed or regenerated plant, or a progeny plant, plant part or seed thereof. If a given mutation, edit, trait or phenotype is recessive, one or more generations or crosses (e.g., selfing) from the initial R0 plant may be necessary to produce a plant homozygous for the edit or mutation so the trait or phenotype can be observed. Progeny plants, such as plants grown from R1 seed or in subsequent generations, can be tested for zygosity using any known zygosity assay, such as by using a SNP assay, DNA sequencing, thermal amplification or PCR, and/or Southern blotting that allows for the distinction between heterozygote, homozygote and wild type plants.

In further embodiments, one or more tissues or cells of a plant developed or regenerated from an explant subjected to particle bombardment or transformation with a DNA encoding a genome editing reagent, or of a progeny plant thereof, or of a plant part or seed of the foregoing, can be screened or selected based on a molecular assay to detect the presence of the edit or mutation, or the site-directed integration of an insertion sequence, transgene, etc. Assays that may be used to detect the presence of an edit or mutation or transgene introduced by site-directed integration include, for example, molecular biology assays, such as Southern and Northern blotting, PCR, FLA, and DNA sequencing; biochemical assays, such as detecting the presence of a protein product, for example, by immunological means (ELISAs and western blots) or by enzymatic function or in vitro analysis. Alternatively, a plant developed or regenerated from an explant subjected to particle bombardment or transformation with a DNA encoding a genome editing reagent, or of a progeny plant or seed thereof, can be screened or selected based on a phenotype or trait, which may be a desired or predicted phenotype or trait.

IV. Definitions

The following definitions are provided to define and clarify the meaning of these terms in reference to the relevant embodiments of the present disclosure as used herein and to guide those of ordinary skill in the art in understanding the present disclosure. Unless otherwise noted, terms are to be understood according to their conventional meaning and usage in the relevant art, particularly in the field of molecular biology and plant transformation.

An "embryo" is a part of a plant seed, consisting of precursor tissues (e.g., meristematic tissue) that can develop into all or part of an adult plant. An "embryo" may further include a portion of a plant embryo.

A "meristem" or "meristematic tissue" comprises undifferentiated cells or meristematic cells, which are able to differentiate to produce one or more types of plant parts, tissues or structures, such as all or part of a shoot, stem, root, leaf, seed, etc.

As used herein, the term "genome editing reagent" refers to any enzyme that can modify a nucleotide sequence in a sequence-specific manner. In some embodiments, a genome editing reagent modifies the genome by inducing a single-strand break. In some embodiments, a genome editing reagent modifies the genome by inducing a double-strand break. In some embodiments, a genome editing reagent comprises a cytidine deaminase. In some embodiments, a genome editing reagent comprises an adenine deaminase. In the present disclosure, genome editing reagents include endonucleases, recombinases, transposases, deaminases, helicases and any combination thereof. In some embodiments, the genome editing reagent is a sequence-specific nuclease.

In one aspect, the genome editing reagent is an endonuclease selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), a guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Cpf1 (also known as Cas12a), Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, CasY, homologs thereof, or modified versions thereof).

In some embodiments, the genome editing reagent comprises a DNA binding domain operably linked to a deaminase. In some embodiments the DNA binding domain is derived from a CRISPR associated protein. In some embodiments, the genome editing reagent comprises uracil DNA glycosylase (UGI). In some embodiments, the deaminase is a cytidine deaminase. In some embodiments, the deaminase is an adenine deaminase. In some embodiments, the deaminase is an APOPEC deaminase. In some embodiments, the deaminase is an activation-induced cytidine deaminase (AID). In some embodiments, the DNA binding domain is a zinc-finger DNA-binding domain, a TALE DNA-binding domain, a Cas9 nuclease, a Cpf1 nuclease, a catalytically inactive Cas9 nuclease, a catalytically inactive Cpf1 nuclease, a Cas9 nickase, or a Cpf1 nickase.

In some embodiments, the genome editing reagent is a recombinase. Non-limiting examples of recombinases include a tyrosine recombinase attached to a DNA recognition motif provided herein is selected from the group consisting of a Cre recombinase, a Gin recombinase, a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

The terms "regeneration" and "regenerating" refer to a process of growing or developing a plant from one or more plant cells through one or more culturing steps.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

As commonly understood in the art, the term "promoter" can generally refer to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present disclosure can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter can also be classified in terms of its origin, such as being heterologous, homologous, chimeric, synthetic, etc.

As used herein, a "plant-expressible promoter" refers to a promoter that can initiate, assist, affect, cause, and/or promote the transcription and expression of its associated transcribable DNA sequence, coding sequence or gene in a plant cell or tissue.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature without human introduction—e.g., the promoter or regulatory sequence has a different origin relative to the associated polynucleotide sequence and/or the promoter or regulatory sequence is not naturally occurring in a plant species to be transformed with the promoter or regulatory sequence. Likewise, a "heterologous promoter" or "heterologous plant-expressible promoter" in relation to an associated polynucleotide sequence, such as a transgene, coding sequence or transcribable DNA sequence, means a promoter or plant-expressible promoter which does not exist adjacent to, and/or operably linked to, the associated polynucleotide sequence in nature without human introduction.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" is used herein to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including" are also open-ended.

For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

The terms "percent identity," "% identity" or "percent identical" as used herein in reference to two or more nucleotide or protein sequences is calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. For example, the "comparison window" can be defined as the region of alignment, in which case the "percent identity" is also referred to as the "alignment percent identity." Accordingly, as used herein, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

According to some embodiments, compositions and formulations of a particle complex or composition may comprise an "effective amount" or an "effective concentration" of a DNA construct or molecule encoding a site-specific nuclease, perhaps along with other components, to edit the genome of a plant. The effective amount or concentration of the particle composition or formulation may depend on a number of factors, such as, for example, the type, size and amount of the particle to which the pre-assembled nuclease composition or formulation is applied, the efficiency of the desired genome editing, the identity and amounts of other ingredients in the composition or formulation, the particular plant species, the type of plant material used (e.g., dry excised explant, a wet excised embryo, etc.), and the specific conditions under which the composition or formulation is applied to the plant material (e.g., temperature, culturing, etc.).

Compositions in some embodiments may further comprise an agriculturally acceptable carrier or material in combination with the particle composition. As used herein, the term "agriculturally acceptable" in reference to a carrier or material means that the carrier or material, as the case may be, (i) is compatible with other ingredients of the particle/nuclease composition at least for the purpose in which the particle/nuclease composition will be used, (ii) can be included in the particle composition to effectively and viably deliver the particle composition to a plant material (e.g., dry excised explant), and (iii) is not deleterious to the plant material to which the composition will be applied (at least in the manner and amount in which it will be applied to, or associated with, the plant material.

All methods described herein can be performed in any suitable order unless otherwise indicated herein or clearly contradicted by context. The use of any and all examples, or exemplary language (e.g., "such as") provided with respect to certain embodiments herein is intended merely to illuminate the present disclosure and does not pose a limitation on the scope of the present disclosure otherwise claimed.

Having described the present disclosure in detail, it will be apparent that modifications, variations, and equivalent embodiments are possible without departing from the spirit and scope of the present disclosure as further defined in the appended claims. Furthermore, it should be appreciated that all examples in the present disclosure including the following are provided as non-limiting examples.

EXAMPLES

Example 1. Preparation of Beads and Carrier Sheets for Bombardment of Soy Explants The following is an example of a protocol for preparation of beads and carrier sheets for bombarding explants. The particles or beads and carrier sheets for bombardment of dry excised embryo explants from soybean seeds using PDS1000 helium particle guns are prepared according to the following protocol. 50 mg of gold or tungsten particles is weighed into a clean DNase/RNase free tube. After being washed by sonication with 1 ml of 100% ethanol, the particles are pelleted by brief centrifugation, and the ethanol is removed. The particles are resuspended in 1 ml of 100% ethanol and stored at −20° C. for later use. Prior to use, the particles are resuspended by sonication. 42 µl of the gold or tungsten particles are transferred to a new tube and pelleted by centrifugation, and the ethanol is removed. 500 µl of sterilized water is added, and the particles are resuspended by sonication. The particles are pelleted by centrifugation, and the water is removed. 25 µl of water is added to the tube, and the particles are washed with a pipette tip before being resuspended by sonication.

Figure 1B:
FIG. 1B is a diagram showing the NotI/I-CeuI restriction fragment excised from a vector having expression cassettes for the gus and aadA marker genes, the Cas9 nuclease and a guide RNA, and which is used for particle bombardment of explants to generated genome edits at the target sites within the PDS gene loci.

In soybean, there are two PDS genes, GmPDS11 (Glyma.11G253000, SEQ ID NO: 1) and GmPDS18 (Glyma.18G003900, SEQ ID NO:2), located on chromosome 11 (chr11) and chromosome 18 (chr18), respectively. Three recombinant DNA constructs each comprising a transcribable DNA sequence encoding one of three guide RNAs, gRNA1, gRNA2 or gRNA3 (SEQ ID NOs: 3-5), respectively, were designed to target conserved regions of GmPDS11 and GmPDS18 as shown in FIG. 1A. Recombinant DNA molecules or fragments comprising an expression cassette or transgene encoding Cas9 under a strong constitutive promoter and a transcribable DNA sequence encoding one of the three gRNAs under a soybean U6 promoter were made as shown in FIG. 1B. As further shown in FIG. 1B, these recombinant DNA molecules also contained expression cassettes or transgenes for GUS and aadA. The recombinant DNA molecules for Cas9, gRNA, GUS and aadA expression were released as linear fragments from a DNA vector comprising the recombinant DNA constructs by NotI and I-CeuI restriction enzymes. The presence of a left border (LB) and right border (RB) are shown since these DNA molecules or fragments were excised from a T-DNA vector, but should not impact these experiments since the fragments are delivered to explant cells via particle bombardment.

The recombinant DNA molecule, construct or fragment, perhaps along with other recombinant DNA molecule(s) and/or non-coding RNA, is/are added to the tube (for example, about 2.6 µg DNA). Ice-cold sterilized water is added shortly after adding the DNA and/or RNA to bring the final volume of the DNA and particles mixture to 245 µl. 250 µl of ice-cold 2.5 M CaCl$_2$) solution and 50 µl of sterilized 0.1 M Spermidine are added shortly after bringing the mixture to volume. This solution is then mixed by low speed vortexing. The tube is incubated on ice for at least 45 minutes to achieve coating of the particles. The solution is mixed every 5-10 minutes for better results in some experiments. The particles are pelleted by low speed centrifugation, for example by using an Eppendorf 5815 microcentrifuge at 800-1000 rpm for 2 minutes. The pellet is washed with 1 ml of ethanol, and the particles are washed with a pipette tip and pelleted by centrifugation. Ethanol is removed, and 36 µl of 100% ethanol is added to resuspend the particles with low speed vortexing. 5 µl of this preparation is used for each bombardment with the helium particle gun. For the electric gun (Accell), this preparation can be modified by combining ten of the 36 µl bead/particle preparations in a scintillation vial and adding 100% EtOH to produce a 20 ml final volume.

The sonication steps above can be performed at 45-55 kHz for 1 min; the centrifugation steps prior to the coating of the beads can be carried out at 5000 rpm (2300 g) on IEC microfuge for 10 seconds; and the centrifugation steps after the DNA coating of beads can be conducted at 1000 rpm (100 g) on IEC microfuge for 2 minutes.

For particle bombardment, a desired amount of tungsten particles (Bio-Rad Laboratories) are resuspended in 50 µl of sterile water after 3 washes with sterile water. Then 2 µl of TransIT® 2020 (Minis Bio LLC) and 30 µl of DNA and/or RNA prepared as provided above was added to the particles, and gently mixed on ice for at least 10 minutes. The coated tungsten particles were then pelleted in a microfuge at 8000×g for 30 seconds and the supernatant fraction was removed. The pellet was resuspended in 180 µl of sterile water by brief sonication. Shortly after sonication, the coated particles were loaded onto 6× macrocarrier (30 µl each) and allowed to air dry for approximately 2-3 hours.

Example 2. Preculturing Soy Explants for Particle Bombardment

The following is an example of a protocol for preculturing explants for bombardment. Dry excised soybean embryo explants are precultured prior to particle bombardment. The mature embryo explants are excised from dry soybean seeds as generally described, for example, in U.S. Pat. No. 8,362, 317. The explants are weighed for blasting, rehydrated for 1 hour in either a 20% PEG4000 (Lynx 3017; see, e.g., U.S. Patent Application Publication No. 2016/0264983) or 10% sucrose medium, and rinsed well. Lynx 1595 (see, e.g., U.S. Patent Application Publication No. 2016/0264983) medium (or Lynx 1595 with 30 ppm Cleary's) can also be used in this step. Approximately 50 explants per plate are precultured on EJW 1 media or EJW 2 media (see, e.g., U.S. Patent Application Publication No. 2016/0264983). TDZ levels in the range of approximately 0.5 ppm to 2 ppm are also used in the EJW (LIMS 4859) media. Explants are precultured for 1-2 days at 28° C. in either a 16/8 hour photoperiod or the dark. The explants may also be precultured for about 3 days.

Example 3. Particle Bombardment of Explants

The following protocol can be used with the PDS1000 helium particle gun. Gun components, such as stop screens, rupture disks and macrocarrier holders, are sanitized for about 1 min using 70% EtOH (or isopropanol for carrier sheets). Rupture disks (e.g., disks for use in the range of approximately 650-2200 psi, including, for example, 1350 psi disks) are loaded into a rupture disk retaining cap and screwed into the gas acceleration chamber. A stop screen is placed on a brass adjustable nest. 5 µl of the helium gun preparation described above is dispensed onto each carrier sheet for each bombardment. Carrier sheets are air dried before they are turned over and placed on top of the stop or retaining screen on the brass nest. A macrocarrier launch assembly is assembled and placed directly under the rupture disk. The gap distance between rupture disk and macrocarrier launch assembly is approximately 1 cm.

Precultured soy explants are positioned and blasted on a target plate medium #42 (TPM42) with meristems facing center and up. The TPM42 medium is prepared by measuring 2 liters of distilled water into a 4 L beaker and adding 16 g of washed agar, which is then autoclaved for 25 minutes to bring the agar into solution. TPM42 may contain 8% carboxymethylcellulose (CMC) for low viscosity (or 2% carboxymethylcellulose (CMC) for high viscosity) and 0.4% of washed agar. The solution is cooled slightly and poured into a 4 L blender, and 320 g CMC (low viscosity) or 80 g CMC (high viscosity) is then added along with 2 L of water. The mixture is blended and transferred to a 4 L plastic beaker, which is then autoclaved for 30 minutes, mixed and divided into four 1 L bottles. The TPM42 solution is then autoclaved for another 25 minutes and cooled to about 60° C. before being poured into plates. About 12 to 15 ml may be poured per 60 mm plate to make about 300 target plates, which may be stored at 4° C. or at −20° C.

The following is an example of a protocol for using an ACCELL electric particle gun. A bead preparation is brought to room temperature and vortexed. A 0.5 Mil 3.2 cm' mylar sheet is placed onto a small plastic dish, optionally in a dehumidifier unit, and 320 µl of the bead prep is placed onto the sheet. Each sheet is air dried. Precultured soy explants are positioned on a TPM42 plate with meristems facing center and up. A blank blast is done first due to inconsistencies in the energy of the first blast. The target is placed over a retaining screen that is placed directly over the carrier sheet. Under a partial helium vacuum (13.5 in Hg), a 10 µL water droplet is vaporized by discharging the capacitor at 17.5-20 kV. The shock wave created by the vaporizing droplet propels the sheet into the retaining screen, which stops most of the mylar but allows the gold beads to enter the soy explant meristems. Between blasts, a drop of mineral oil is suspended between points and then removed to clean them. 10 µL of water is suspended between points as before. The arc chamber is covered with PVC block, a mylar sheet is placed on the square opening, and the screen hood is placed over the sheet and points. The screen is aligned over the sheet. The target dish is placed upside down over the retaining screen, such that the meristems are oriented above it, and weight is placed on the dish. The apparatus is covered with a bell jar and the vacuum is engaged. After 15 seconds, the vacuum reads 13.5 in Hg, and the gun is discharged.

Example 4. Culturing of Explants Following Particle Bombardment

Bombarded explants are surface plated onto EJW 1 media overnight (other pre-culturing media may also be used). In one example, plates are incubated at 28° C. with a 16/8 hour photoperiod. The explants are surface plated or embedded onto 50-500 ppm spectinomycin-containing B5 media (LIMS 3485 with modified spectinomycin levels; see, e.g., U.S. Patent Application Publication No. 2016/0264983), and kept at 28° C. with a 16/8 hour photoperiod throughout the regeneration process. In one example, 250 ppm spectinomycin in B5 media is used. The presence of the aadA selectable marker gene provides resistance or tolerance to spectinomycin as a selection agent. The 24.5 g of B5 custom media mix includes 3.21 g Gamborg's B5 medium, 20 g sucrose, and 1.29 g calcium gluconate. Cultures are monitored for shoots/greening and subcultured as necessary.

Example 5. Identification of Edited PDS Mutants after Particle Delivery and Regeneration The equivalent of either 0.02 or 0.04 pmoles per shot of the DNA fragment shown in FIG. 1B was loaded onto particles for biolistic delivery. Plants regenerated from the bombarded explants were screened for the presence of the aadA marker. Plants positive for the aadA marker gene as determined by real-time quantitative PCR were further tested for the presence of edits due to co-delivery of the recombinant DNA expressing Cas9 and gRNA targeting the PDS gene loci. Genomic DNA was extracted from leaf samples of regenerated plantlets after 2 weeks post-bombardment, and the presence of an edit at one or both PDS loci was detected by Fragment Length Analysis (FLA). FLA is a PCR based molecular analysis that compares variations in PCR fragment length to amplicons from a wild-type reference to identify samples having one or more mutations relative to the wild-type reference. PCR reactions were carried out using a 5' FAM-labeled primer, a standard primer and a Phusion™ polymerase (Thermo Fisher Scientific) according to manufactures instructions, to generate 200 to 500 bp PCR fragments. FLA primers for GmPDS genes as set forth in SEQ ID NOs: 6 and 7 give rise to a 428 bp PCR fragment for GmPDS11 and a 384 bp PCR fragment for GmPDS18. PCR fragments that differ from these expected sizes are considered mutant or edited alleles. As shown in FIG. 1, the editing frequencies observed following bombardment ranged from 17.6% to 42.5% at the GmPDS loci.

TABLE 1

Mutation frequency at GmPDS loci with different Cas9/gRNA combinations.

| Cas9/gRNA combination | # aadA positive samples | # edited samples by FLA | Editing frequency (%) |
| --- | --- | --- | --- |
| Cas9 and gRNA1 (SEQ ID NO: 3) | 153 | 27 | 17.6 |
| Cas9 and gRNA2 (SEQ ID NO: 4) | 214 | 91 | 42.5 |
| Cas9 and gRNA3 (SEQ ID NO: 5) | 107 | 39 | 36.4 |

Example 6. Identification of Site Directed Integration (SDI) Events into PDS Locus on Chromosome 18

Delivery of Cas9 and a gRNA with a donor template comprising an insertion sequence can lead to site directed integration (SDI) of the insertion sequence at the target site for the gRNA. In some cases, a DNA molecule or fragment encoding one or more of the genome editing components (e.g., site-specific nuclease, gRNA, and/or marker gene) may itself also serve as a template for site-directed integration. Even if the DNA molecule or fragment does not contain homology sequence(s) for homology-mediate repair, insertion of the DNA molecule or fragment can occur through non-homologous end joining (NHEJ). Example 5 above shows that numerous genome edits are produced through particle bombardment with the DNA fragment provided in FIG. 1B. The DNA fragment in FIG. 1B used to deliver the genome editing components in this example could also be inserted at the gRNA/Cas9 target cut site through NHEJ. In this experiment, two integration events were detected at the gRNA target site in the DNA fragment in FIG. 1B.

Figure 1C:
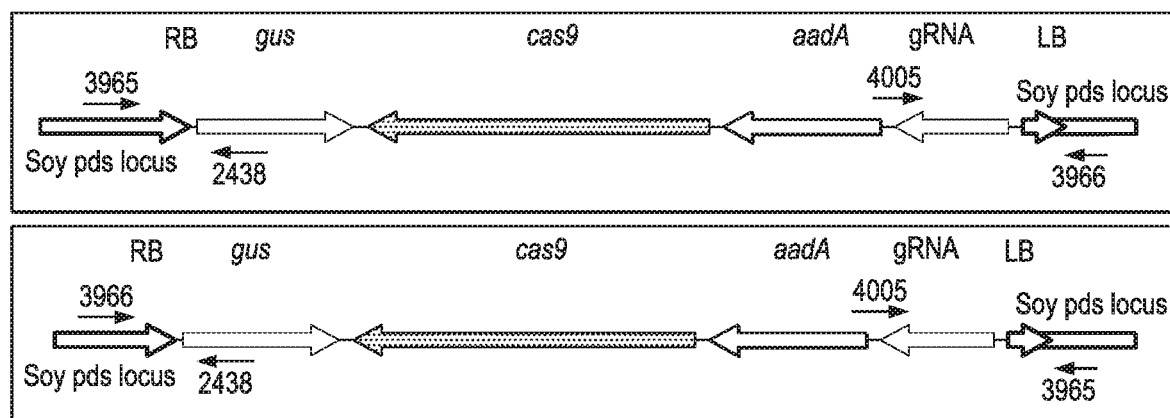
FIG. 1C is a diagram showing the different possible orientations for insertion of the full NotI/I-CeuI restriction fragment into the PDS gene locus with binding sites for PCR primers (3965, 3966, 2438, and 4005) shown for each orientation.

Four PCR assays were established to detect the presence of the insertion sequence, which could occur in two different orientations as illustrated in FIG. 1C. Beads were loaded with either 0.02 or 0.04 pmoles per shot of the DNA fragment from Example 5 encoding Cas9 and gRNA2 (SEQ ID NO: 4). PCR using primers 3965 (SEQ ID NO: 8) and 2438 (SEQ ID NO: 9) and/or PCR using primers 4005 (SEQ ID NO: 10) and 3966 (SEQ ID NO: 11) were used to detect one orientation of an SDI insertion of the DNA fragment, while PCR using primers 3966 and 2438, and/or PCR using primers 4005 and 3965 were used to detect the other SDI orientation as shown in FIG. 1C.

Figure 2:
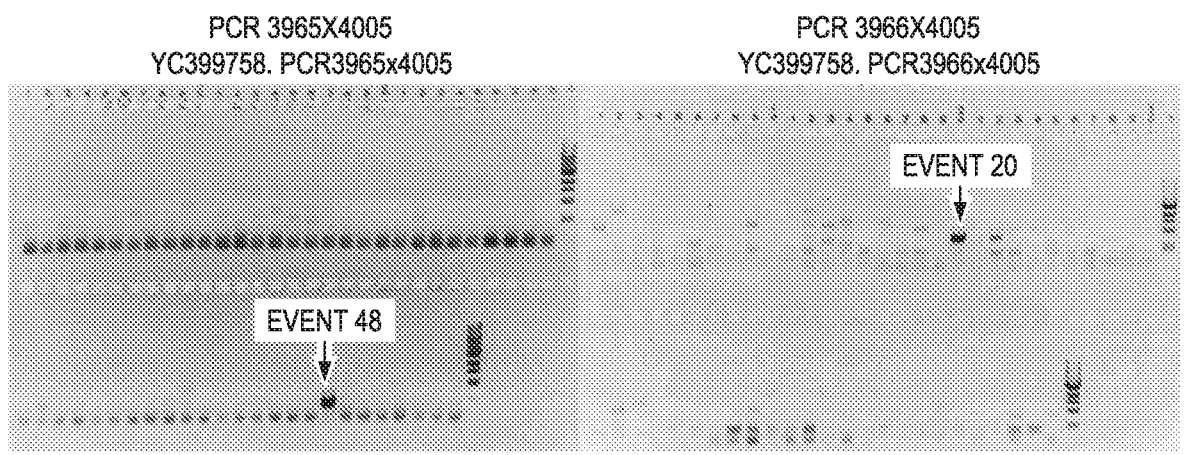
FIG. 2 is an image of a gel showing the PCR products generated using different primer pairs (3965 and 4005, or 3966 and 4005), showing two site-directed integration (SDI) events (Event #20 and Event #48) among the edited samples tested.

Events #48 and #20 containing an insertion of at least a portion of the DNA fragment were found by PCR (see FIG. 2), which were further confirmed by sequencing through the integration junctions. Event #20 has an intact NotI sequence at one end of the insertion, but the other I-CeuI end of the fragment was not detected by PCR, indicating that a deletion or structural change occurred at this end that prevented PCR amplification. Event #20 occurred at the PDS locus on chromosome 18, and Taqman analysis further revealed that more than 4 copies of all or part of the DNA fragment were integrated at the site. Event #48 was determined to have a deletion at one end (I-CeuI end) of the insertion as detected by PCR with primers 3966 and 4005. The other end of the Event #48 insertion was not detected by PCR, indicating that a deletion or structural change occurred at this end that prevented PCR amplification. Similar to Event #20, Event #48 occurred at the PDS locus on chromosome 18, and Taqman analysis further revealed that more than 4 copies of all or part of the DNA fragment were integrated at the site The number and frequency of SDI events in the GmPDS (Chr18) locus are provided in Table 2. Mutations in the PDS genes can cause a white colored leaf phenotype, which may indicate that an edit to a PDS gene may have occurred and/or is present in those tissues.

TABLE 2

Identification of SDI events and observed SDI frequency.

| Coated DNA | pmole/shot | # Green Samples | # White Samples | Total Samples | # SDI events | SDI Frequency (%) |
| --- | --- | --- | --- | --- | --- | --- |
| Cas9 & gRNA2 | 0.02 | 10 | 14 | 24 | 1 | 4.17 |
| Cas9 & gRNA2 | 0.04 | 23 | 8 | 31 | 1 | 3.23 |

Example 7. Delivery of Cpf1, gRNA and ssDNA into Mature Seed Explants

LbCpf1 shows a preference for the TTTV PAM sequence, therefore, target sites GmTS1 was chosen based on the occurrence of the appropriate PAM sequence upstream of each target sequence. Guide RNA was designed to guide the LbCpf1 protein to the target site. Recombinant DNA for expressing LbCpf1 protein, guide RNAs and aadA was cloned.

Furthermore, a 5' TEG modified 70-bp long ssDNA (single strand DNA) template was designed. The TEG modified ssDNA template was ordered from Integrated DNA Technologies (IDT, product 1184, Mod Code: /5Sp9/). This template has a 10 bp signature sequence containing a BamHI recognition sequence flanked by a 30-bp 5' homology arm and 30-bp 3' homology arm respectively that are designed to be identical to the DNA sequence flanking the GmTS1 site. The corresponding wildtype sequence at the GnTS1 site has an 8-bp endogenous sequence between the 5' and 3' homology arms. This single-stranded DNA template (ssDNA template) was added to the recombinant DNA for expressing LbCpf1 protein, crRNAs and aadA. Specifically, 80 pmol of ssDNA template, 0.8 pmol of the recombinant DNA were coated onto 0.6 um gold particles (Bio-Rad; ~66 ug/shot)) using TransIT-2020 as coating reagent. The mixture was kept on ice for >=15 min with gentle mixing every 5 min. Coated gold particles were pelleted by brief centrifugation, and the supernatant was removed. The coated gold particles were re-suspended and washed with 1 mL 100% pre-chilled ethanol followed by a brief centrifugation to remove the ethanol. The coated gold particles were resuspended into 30 ul 100% pre-chilled ethanol, then loaded onto microcarrier discs (5 ul per shot) and dried for 10 mins.

Dry excised soybean embryo explants were rehydrated for 1 hr in LIMS 3990 (B5 custom medium containing 1 gram/L KNO3, 0.03 gram/L Clearys 3336 WP, 3.9 gram/L MES, 30 gram/L, at pH to 5.6), rinsed well with sterile H2O, and cultured in medium LIMS 4859 at 28° C. with 16/8 hour photoperiod for 1 day. Bombardment of these precultured mature soybean embryo explants was carried out according to Example 3. After bombardment, the embryo explants were transferred onto medium LIMS 4859 and cultured at 28° C. or 37° C. in dark for two days.

As shown in Table 3, at 28° C. across 15 experiments, the mutations (small insertion or deletion around the designed Cpf1 cutting site) rate was 41.7% and the perfect template editing (having the 10 bp signature sequence containing a BamHI recognition sequence franked by the 5' and 3' junctions defined by the homology arms) rate was 0.25%. At 37° C. across 15 experiments, the mutations (small insertion or deletion) rate was 49.9% and the perfect template editing (having the 10 bp signature sequence containing a BamHI recognition sequence franked by the 5' and 3' junctions defined by the homology arms) rate was 0.35%.

TABLE 13

Temperature effect on editing rate

| Temperature | Number of Experiments | Mutation rate (indels) % | Perfect template editing rate (%) |
|---|---|---|---|
| 28° C. | 15 | 41.7 | 0.25 |
| 37° C. | 15 | 49.9 | 0.35 |

While the present invention has been disclosed with reference to certain embodiments, it will be apparent that modifications and variations are possible without departing from the spirit and scope of the present invention as disclosed herein and as provided by the appended claims. Furthermore, it should be appreciated that all examples in the present disclosure, while illustrating embodiments of the invention, are provided as non-limiting examples and are, therefore, not to be taken as limiting the various aspects so illustrated. All references cited in the present disclosure are incorporated herein by reference in their entirety. The present invention is intended to have the full scope defined by the present disclosure, the language of the following claims, and any equivalents thereof. Accordingly, the drawings and detailed description are to be regarded as illustrative and not as restrictive.

The invention claimed is:

1. A method of editing a genome of a plant, comprising:
   a) excising an embryo from a dry mature plant seed, thereby producing a dry-excised mature plant embryo explant;
   b) delivering to the dry-excised mature plant embryo explant via particle bombardment a recombinant DNA construct comprising a sequence encoding a site-specific nuclease, wherein
      i) the site-specific nuclease is a ribonucleoprotein;
      ii) the site-specific nuclease is Cas1, Cas1B, Cas2, Cas3, Cas4, Cas5, Cas6, Cas7, Cas8, Cas9, Csn1, Csx12, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, CasZ, an Argonaute protein, or a homolog or modified version thereof;
      iii) the site-specific nuclease is not a guided nuclease; or
      iv) the site-specific nuclease is a meganuclease, a zinc-finger nuclease (ZFN), a recombinase, a transposase, or a transcription activator-like effector nuclease (TALEN), and
   wherein the sequence encoding the site-specific nuclease is operably linked to a plant-expressible promoter,
   c) culturing the dry-excised mature plant embryo explant after bombardment for at least two days in dark at about 37° C.; and
   d) regenerating a plant from the dry-excised mature plant embryo explant without forming an embryogenic callus or callus culture from the dry-excised mature plant embryo explant,
   wherein the regenerated plant comprises an edit or site-directed integration at or near the target site of the site-specific nuclease in the genome of at least one cell of the regenerated plant.

2. The method of claim 1, wherein
   a) said particle is a tungsten, platinum or gold particle;
   b) said particle has a size of between about 0.5 μm and about 1.5 μm;
   c) said particle has a size of about 0.6 μm, about 0.7 μm, or about 1.3 μm;
   d) a plurality of particles coated or applied with the recombinant DNA construct are delivered to the dry-excised mature plant embryo explant via particle bombardment; or
   e) the amount of particles delivered to the dry-excised mature plant embryo explant is between about 50 μg and about 5000 μg, or between about 50 μg and about 2000 μg, or between about 50 μg and about 1000 μg, or between about 50 μg and about 500 μg, or between about 100 μg and about 500 μg.

3. The method of claim 1, further comprising:
   c) identifying a regenerated plant having at least one cell comprising the edit or site-directed integration at or near the target site of the site-specific nuclease.

4. The method of claim 3, wherein the identifying step comprises:
   i) identifying a regenerated plant having the edit or site-directed integration based on a phenotype or trait; or
   ii) identifying a regenerated plant having the edit or site-directed integration based on a molecular assay.

5. The method of claim 1, wherein the particle is further coated or applied with a guide RNA or with a second recombinant DNA construct or molecule.

6. The method of claim 1, wherein said Cas9 protein is from *Streptococcus pyogenes*.

7. The method of claim 1, wherein the delivering step further comprises delivering a second recombinant DNA construct or molecule to the dry-excised mature plant embryo explant.

8. The method of claim 7, wherein a) the second recombinant DNA construct or molecule is a donor template; b) the second recombinant DNA molecule comprises a marker gene; c) the second recombinant DNA construct or molecule comprises a donor template region and a transgene comprising a coding sequence or a transcribable DNA sequence, wherein the transgene is located outside of the donor template region of the second recombinant DNA construct or molecule; or d) the second recombinant DNA construct or molecule comprises a transcribable DNA sequence encoding a guide RNA, wherein the transcribable DNA sequence is operably linked to a plant-expressible promoter.

9. The method of claim 8, wherein a) the donor template comprises a homology sequence comprising a mutation for introduction of the mutation in the genome of the plant at or near the target site of the site-specific nuclease through template-mediated repair; or b) the donor template comprises an insertion sequence and at least one homology sequence for integration of the insertion sequence into the genome of the plant at or near the target site of the site-specific nuclease.

10. The method of claim 9, wherein the insertion sequence comprises a transgene comprising a coding sequence or a transcribable DNA sequence operably linked to a plant-expressible promoter.

11. The method of claim 10, wherein the transgene comprises a gene of interest, a protein coding sequence, a transcribable DNA sequence encoding a non-coding RNA molecule, or a marker gene.

12. The method of claim 8, wherein said marker gene a) is a selectable marker gene; b) is a screenable marker gene; or c) comprises an adenylyltransferase (aadA) gene, a neomycin phosphotransferase (nptII) gene, a hygromycin phosphotransferase (hpt, hph or aph IV), 5-enolpyruvylshikimate-3-phosphate synthase (EPSPS) gene, a dicamba monooxygenase (DMO) gene, a bialaphos resistance (bar) or phosphinothricin N-acetyltransferase (pat) gene, a green fluorescent protein (GFP), or a β-glucuronidase (GUS) gene.

13. The method of claim 1, wherein a) the recombinant DNA construct further comprises a marker gene; b) the recombinant DNA construct further comprises a transcribable DNA sequence encoding a guide RNA, wherein the transcribable DNA sequence is operably linked to a second plant-expressible promoter; or c) the recombinant DNA construct further comprises a donor template region.

14. The method of claim 13, wherein said marker gene a) is a selectable marker gene, b) is a screenable marker gene; or c) comprises an adenylyltransferase (aadA) gene, a neomycin phosphotransferase (nptII) gene, a hygromycin phosphotransferase (hpt, hph or aph IV), 5-enolpyruvylshikimate-3-phosphate synthase (EPSPS) gene, a dicamba monooxygenase (DMO) gene, a bialaphos resistance (bar) or phosphinothricin N-acetyltransferase (pat) gene, a green fluorescent protein (GFP), or a β-glucuronidase (GUS) gene.

15. The method of claim 13, wherein a) the donor template region comprises a homology sequence comprising a mutation for introduction of the mutation in the genome of the plant at or near the target site of the site-specific nuclease through template-mediated repair; or b) the donor template region comprises an insertion sequence and at least one homology sequence for integration of the insertion sequence into the genome of the plant at or near the target site of the site-specific nuclease.

16. The method of claim 15, wherein the insertion sequence comprises a transgene comprising a coding sequence or a transcribable DNA sequence operably linked to a plant-expressible promoter.

17. The method of claim 16, wherein the transgene comprises a gene of interest, a protein coding sequence, a transcribable DNA sequence encoding a non-coding RNA molecule, or a marker gene.

18. The method of claim 1, further comprising:
e) selecting a regenerated plant having a marker gene, wherein the marker gene is co-delivered with the recombinant DNA molecule.

19. The method of claim 18, wherein the marker gene is a selectable marker gene.

20. The method of claim 19, wherein a) the selecting step comprises treating the dry-excised mature embryo explant, or a shoot and/or root culture or plantlet regenerated therefrom, with a selection agent; or b) the selectable marker gene is an adenylyltransferase (aadA) gene.

21. The method claim 1, wherein said plant is a dicot plant.

22. The method of claim 21, wherein said plant is a soybean plant.

23. The method of claim 1, wherein the dry-excised mature embryo explant comprises, prior to the delivering step, one or more of the following: (i) a guide RNA (gRNA), (ii) a polynucleotide comprising a transgene or marker gene, (iii) a polynucleotide comprising a transgene encoding a non-coding RNA molecule or guide RNA, and/or (iv) a donor template.

24. The method of claim 1, wherein a) the dry-excised mature embryo explant has a moisture content within a range from about 3% to about 25%; or b) the dry-excised mature embryo explant is excised from a plant seed having a moisture content within a range from about 3% to about 25%.

25. The method of claim 7, wherein the delivering step comprises delivering a DNA molecule or vector comprising the recombinant DNA construct and the second recombinant DNA construct to the dry-excised mature plant embryo explant.

\* \* \* \* \*